United States Patent
de Corral

(10) Patent No.: US 6,276,195 B1
(45) Date of Patent: Aug. 21, 2001

(54) THREE CAPILLARY FLOW-THROUGH VISCOMETER

(75) Inventor: Jose Luis de Corral, Hopedale, MA (US)

(73) Assignee: Waters Investments Limited ( * ) Notice: Subject to any disclaimer, the term of this patent is extended or adjusted under 35 U.S.C. 154(b) by 0 days.

(21) Appl. No.: 09/702,478

(22) Filed: Oct. 31, 2000

Related U.S. Application Data

(63) Continuation of application No. 09/196,614, filed on Nov. 19, 1998, now Pat. No. 6,158,271, which is a continuation of application No. PCT/US97/03162, filed on Feb. 2, 1997, and a continuation-in-part of application No. 08/608,587, filed on Feb. 28, 1996, now Pat. No. 5,637,790.

(51) Int. Cl.⁷ .............................. G01N 11/04; G01N 9/32; G01N 11/08
(52) U.S. Cl. .................... 73/54.05; 73/54.04; 73/863.03; 73/61.56; 73/61.57; 73/861.49
(58) Field of Search ................................ 73/54.05, 54.06, 73/54.04, 54.02, 861.49, 861.51, 863.58, 863.03, 864.72, 864.73, 863.12, 61.56, 61.57

(56) References Cited

U.S. PATENT DOCUMENTS

| | | | |
|---|---|---|---|
| T960,004 * | 7/1977 | Neville | 73/55 |
| 3,086,386 * | 4/1963 | Kapff | 73/23 |
| 3,138,950 * | 6/1964 | Welty et al. | 73/55 |
| 3,798,960 * | 3/1974 | Glass | 73/55 |
| 3,808,877 * | 5/1974 | Blair | 73/55 |
| 3,908,442 * | 9/1975 | Chmiel | 73/55 |
| 3,938,369 * | 2/1976 | de Bok | 73/55 |
| 4,384,472 * | 5/1983 | Journier | 73/30 |
| 4,463,598 * | 8/1984 | Haney | 73/55 |
| 4,578,990 * | 4/1986 | Abbott et al. | 73/55 |
| 4,627,271 * | 12/1986 | Abbott et al. | 73/55 |
| 4,876,882 * | 10/1989 | Yau | 73/55 |

* cited by examiner

Primary Examiner—Hezron Williams
Assistant Examiner—David J. Wiggins
(74) Attorney, Agent, or Firm—Brian Michaelis

(57) ABSTRACT

A method and apparatus for measuring the viscosity of a sample solution which comprises an input tube for transporting a sample solution flow towards a splitter for diverting input flow into two distinct flow streams where three capillary tubes are located in the two flow streams placed downstream from the flow splitter, where each flow stream has one or two capillary tubes a delay volume, and a flow through transducer having hydraulic connections placed in one stream or in two streams used for measuring the pressure difference across the capillary tubes.

9 Claims, 13 Drawing Sheets

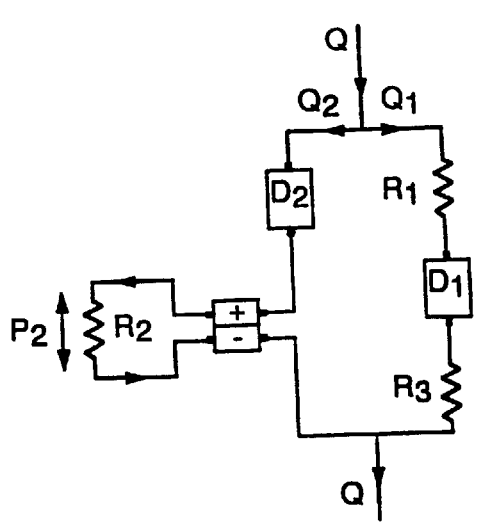
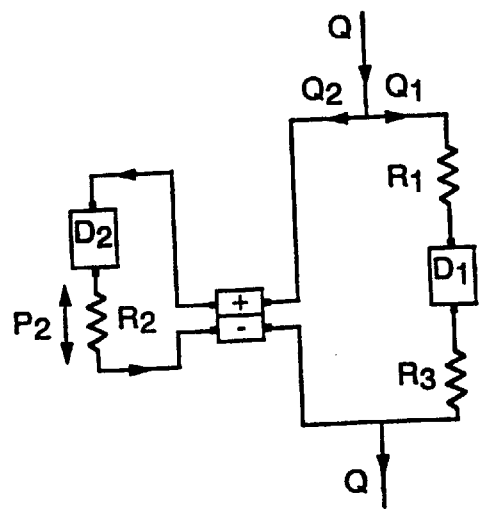
FIG. 4a              FIG. 4b
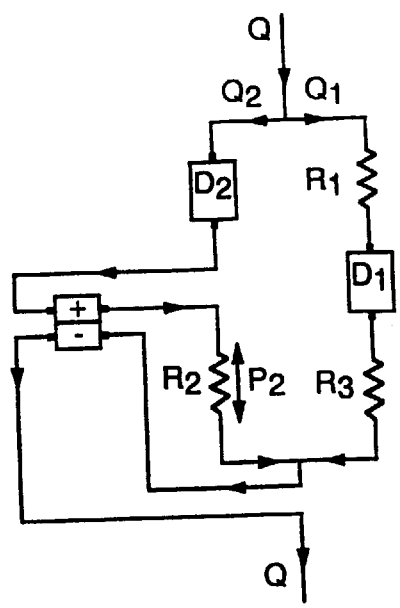
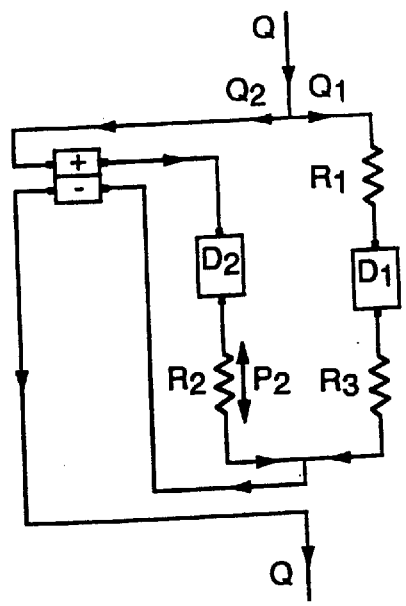
FIG. 4c              FIG. 4d

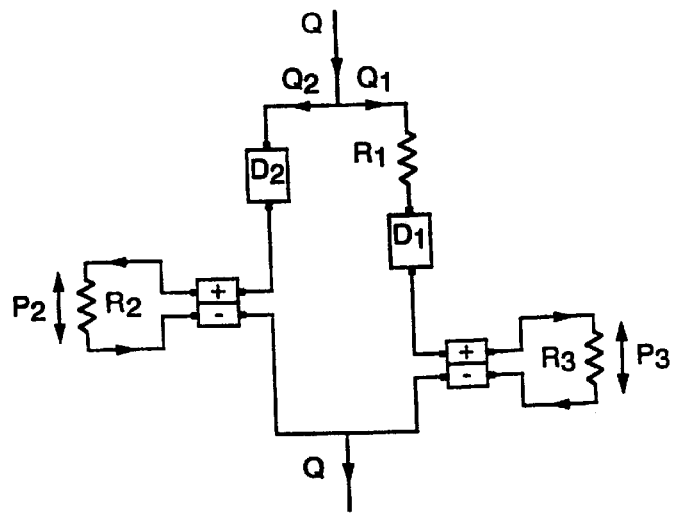
FIG. 6a
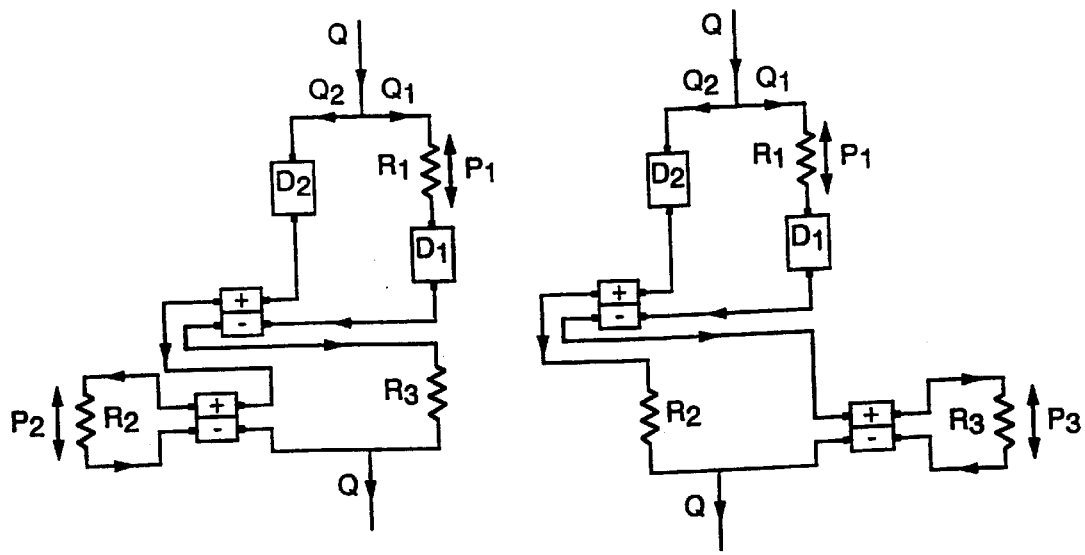
FIG. 6b
FIG. 6c

THREE CAPILLARY FLOW-THROUGH VISCOMETER

This application is a continuation of commonly owned, U.S. application Ser. No. 09/196,614, filed on Nov. 19, 1998 entitled THREE CAPILLARY FLOW-THROUGH VISCOMETER, incorporated in its entirety into the present application which is a continuation of application PCT/US97/03162 filed Feb. 2, 1997 and a continuation in part of application Ser. No. 08/608,587 filed Feb. 28, 1996 now U.S. Pat. No. 5,637,790.

FIELD OF THE INVENTION

This invention pertains to the field of viscosity measurement. In particular, it pertains to the field of capillary viscometers; specifically, a novel three-capillary viscometer used to measure the viscosity of a solution is disclosed herein. This invention also pertains to the field of digital signal processing, and more particularly it pertains to methods for measuring viscosity and relative flow that have direct application in viscosity detectors or viscometers, used in chromatography to measure the viscosity of fluids.

DESCRIPTION OF THE PRIOR ART

The measurement of a fluids' viscosity is a very important part of Liquid Chromatography (LC). Particularly, in Size Exclusion Chromatography (SEC) a viscometer detector in combination with a concentration detector, provides important information about molecular weight in polymer analysis.

The most basic capillary type viscometer is the single capillary viscometer. It is based on the idea that when a fluid goes through a capillary tube, the pressure drop across the capillary is proportional to the fluid viscosity and flow. They are related according to Poiseuille's law:

$$P = R \cdot \eta \cdot Q$$

$$R = \frac{8}{\pi} \cdot \frac{L}{r^4}$$

Where:

P Pressure drop across capillary

R Capillary geometrical restriction $\eta$ Viscosity of solution

Q Solution flow rate

L Capillary length

R Capillary inside radius

In practice, a pressure transducer is placed across the capillary to measure the pressure drop. If the flow is constant, the pressure is proportional only to the solution viscosity. This viscometer is very simple but has the disadvantage that the pressure output is also proportional to the solution flow rate. Therefore, any small disturbance in the fluid flow through the capillary generates a pressure drop of the same magnitude, or even greater, than the pressure drop caused by the solution viscosity.

The flow through the capillary depends primarily on the pumping system flow, and on the temperature changes in the whole system. All of the slow and fast flow disturbances created by the pump are clearly detected by the viscometer. Also, any temperature change anywhere in the chromatograph creates solution expansions and contractions, that in turn create flow disturbances that are also detected by the viscometer. Even the viscosity changes due to the injected sample, can potentially create a flow disturbance. If the pumping system cannot react quickly to the varying pressure load created by the sample passing through the system, it also causes flow disturbances in the viscometer.

All of these issues impose extremely rigid requirements on the pump and the whole system, to obtain good performance out of the single capillary viscometer. The pumping system should deliver an extremely precise and constant flow, free of any slow drifts or fast transients such as those normally associated with the repetitive pump action. The entire system should be maintained at constant temperature to eliminate flow errors due to temperature changes. The volumes and tubing sizes in the system should be carefully considered to prevent flow disturbances due to the sample viscosity.

There are several types of capillary viscometers. The single-capillary viscometer discussed above was originally described in U.S. Pat. No. 3,837,217. Another single capillary design is shown in U.S. Pat. No. 4,286,457. The single capillary design suffers from the major drawbacks described, including temperature sensitivity, sensitivity to minor pump fluctuations, and general intolerance to minor system disturbances such as injection.

A multiple capillary design is described in U.S. Pat. No. 4,463,598 (Haney). Haney discloses a bridge-type viscosity measuring device having two separate branches. Each branch has two capillaries arranged in series. The branches are connected at the top and bottom by common input and output lines. A bridge having a dead-ended pressure transducer connects across the branches in their middle between the first and second capillaries, thereby measuring differences in pressure across the two branches at those points. Under normal operation (viscosity the same in both branches) there is fluid flow down both branches encountering the same resistance and hence no pressure difference. In operation, a fluid of different viscosity is introduced into one branch, and as it enters the capillary a pressure differential begins to build until a maximum is reached when the sample is entirely within the capillary. The pressure difference is then measured via the transducer and mathematical operations give relative viscosity of the two solutions. A key drawback to this design is the necessity to balance the capillaries so that they are substantially equal in resistance.

U.S. Pat. Nos. 4,627,271 and 4,578,990 to Scot D. Abbott and Wallace W. Yau (Abbott et al.) describe a differential pressure capillary viscometer which may be used to measure viscosity independent of flow rate and temperature fluctuations. These patents disclose a viscometer in which a solvent is pumped from a reservoir into a system comprising a solute injection valve upstream of two capillary tubes which are separated by a large depository column which is used to trap solute, so that only solvent flows through the second capillary tube. Changes in pressure across both capillary tubes are measured and converted into electrical signals, which are fed to a differential logarithmic amplifier. The output signal of the differential logarithmic amplifier is related to the natural logarithm of the relative viscosity. Both the inherent and intrinsic viscosities may be related mathematically to the experimentally measured value for the relative viscosity. Although the apparatus disclosed in these patents provides a viscosity measurement which is independent of flow rate and temperature fluctuations, it is, however, sensitive to fast flow transients or high frequency flow pulses, like those caused by the pumping system or the sample injector.

Yau, U.S. Pat. Nos. 4,793,174, and 4,876,882 disclose a similar apparatus, with the exception that the large depository column is eliminated, and a small separation volume is placed between the two capillaries instead. This effectively eliminates the delay associated with the large depository column, while retaining independence of flow rate and temperature fluctuations. However, the apparatus described in these patents requires closely matched capillaries for best performance, and they are also sensitive to fast flow transients and high frequency flow pulses.

Furthermore, all the previous designs use pressure transducers with "dead-end" connections, that must be purged for correct operation. This creates additional problems as described hereinafter. Therefore, all of these designs have some deficiencies, and to date none show robust and accurate operation. There is a need for an improved design for capillary viscometers.

SUMMARY OF THE INVENTION

The invention is an apparatus for measuring the viscosity of a sample solution, comprising an input tube for transporting the sample solution flow Q; a flow splitter in fluid communication with and downstream from the input tube, for diverting the flow Q into flow streams Q1 and Q2 ; a first capillary tube R1 located in stream Q1 downstream from the flow splitter; a first delay volume D1 located in stream Q1 downstream from capillary R1; a second delay volume D2 located in stream Q2 downstream from the flow splitter; a second capillary tube R2 located in stream Q2 and downstream from delay volume D2; a third capillary tube R3 located in stream Q1 and downstream from delay volume D1; a first flow-through transducer T1 having hydraulic connections located in stream Q1 and Q2, the connections being located so as to measure the pressure difference across capillary R1, transducer T1 generating a signal proportional to the pressure difference across capillary R1; a second flow-through transducer T2 having hydraulic connections located in stream Q2, the connections being located so as to measure the pressure difference across capillary R2, transducer T2 generating a signal proportional to the pressure difference across capillary R2; and signal handling means for processing the signals from transducers T1 and T2 and generating thereby the relative viscosity information for the sample solution, and the relative flow information for the sample solution flow.

It is an object of the invention to provide separately Relative Viscosity and Relative Flow information.

It is another object of the invention to provide a flow-through viscometer design in which the solution is always flowing through all of its components without any fluid dead ends, and without the purge requirements of other viscometer designs.

It is a further object of the invention to provide a relative viscosity output that is independent of both low and high frequency components of the viscometer flow.

It is a further object of the invention to provide a capillary viscometer that does not require matching or balancing the capillaries' restriction in any way, therefore the relative viscosity output is independent of the capillaries' restriction tolerance.

It is a further object of the invention to provide a method for compensating for non-linearities in pressure to flow relationships.

It is a further object of the invention to provide a method for compensating for the effects of pressure transducers having different fluidic properties.

In further accord with the present invention the problems of fast flow disturbances are solved via a digital signal processing method that relates the dynamics of the two pressure measurements normally involved in multiple-capillary viscometer designs, which can be used with any viscometer having two or more capillaries and at least two pressure transducers. Using this technique, the viscometer detector output is independent of both low and high frequency components of the viscometer flow. The viscometer performance is enhanced, significantly without using special pumping systems or any flow smoothing devices.

BRIEF DESCRIPTION OF THE DRAWINGS

FIGS. 4a through 4f are schematic diagrams of six possible ways to measure the pressure across $R_2$ ($P_2$) with the transducer connected flow-through and without causing any bandspreading in the distribution peak going through $R_1$.

FIGS. 6a through 6c are schematic diagrams of three embodiment examples from the 120 distinct possible embodiments of the Invention.

DETAILED DESCRIPTION OF THE INVENTION

Figure 1:
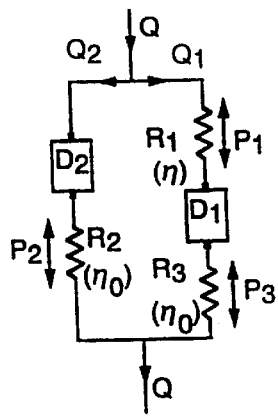
FIG. 1 is a schematic diagram of the invention, to show the relative connection of the capillaries and delay volumes.

The invention provides some very important improvements to viscosity detection that are only addressed by the present invention. These are pointed out in the following description of the main benefits of the invention.

Relative Viscosity and Relative Flow Outputs

The viscometer of the present invention provides separately Relative Viscosity information, and Relative Flow information. The Relative Viscosity ($\eta_{rel}$) is the ratio of the solution viscosity ($\eta$) over the solvent viscosity ($\eta_0$) as a function of time, while the solution is passing through the viscometer. The Relative Flow ($Q_{rel}$) is the ratio, also as a function of time, of the solution flow (Q) over the solvent flow at a particular reference time ($Q_0$).

The Relative Viscosity information finds immediate use in Size Exclusion Chromatography as a means to obtain the "Specific Viscosity" ($\eta_{sp}$), the "Inherent Viscosity" ($\eta_{inh}$), the "Reduced Viscosity" ($\eta_{red}$), and the "Intrinsic Viscosity" ($\eta_{intr}$) (C is the concentration of polymer solution) according to the following formulas:

$$\eta_{rel} = \frac{\eta}{\eta_0} \qquad \eta_{sp} = \eta_{rel} - 1 \qquad \eta_{inh} = \frac{ln\eta_{rel}}{C} \qquad \eta_{red} = \frac{\eta_{sp}}{C}$$

$$\eta_{intr} = \lim_{C \to 0} \eta_{inh} = \lim_{C \to 0} \eta_{red}$$

Relative Flow

The Relative Flow information can also be used in size exclusion chromatography, to correct retention time fluctuations due to flow fluctuations. This provides better retention time repeatability between consecutive sample injections, which is a fundamental need in this analytical technique. The retention time correction can be applied not only to the Relative Viscosity chromatogram, but also to other chromatograms from other detectors connected in series with the viscometer. In addition to this, the relative flow signal, is a valuable diagnostic tool in determining the correct functioning of the pumping system.

The methods and apparatus for determining viscosity as known in the prior art, provide a viscosity value that is partially or fully independent of viscometer flow, but lacks the capability of providing a flow related value. Therefore, the prior art must be used with a pumping system that delivers a constant flow, to guarantee retention time repeatability throughout an entire sequence of samples. With the Relative Flow value, the viscometer of the present invention can tolerate errors in the delivered flow during the sequence of samples.

Flow-through

The present invention is a flow-through viscometer design in which the solution is always flowing through all of its components without any fluid dead ends, and without the purge requirements of other viscometer designs.

In prior an viscometers that use differential pressure transducers, including the single capillary viscometer, the solvent inside the transducers is stagnant and it serves as pressure transmitting media only. Each side of the transducer is connected to the flow path through connecting tubing and "T" unions.

The solvent inside the transducer has to be purged from time to time to remove contaminants, as well as every time the type is changed, to maintain good pressure transmission of solvent inside the transducer. The purge can be done manually or automatically with solenoid valves. Manual purge presents safety issues due to the hazardous solvents normally used. Automatic purge presents cost and reliability issues due to the valves and controls required.

In the present invention, as the solvent is always flowing through the transducer cavities, a transducer purge is not required, and the transducer is always in the best operating condition.

Viscosity Output Independent of Fast Flow Changes

Prior art viscometers provide a viscosity output that is independent of low frequency flow components, like flow drifts and slow flow fluctuations. They are, however, sensitive to high frequency flow components like pulses of the pumping system, or fast flow fluctuations like the sample injector transients of a chromatography system. These prior art viscometer designs require smooth pumping systems or additional devices to decrease or filter these fast flow disturbances. The viscometer of the present invention provides a relative viscosity output that is independent of both low and high frequency components of the viscometer flow. Therefore, it is not necessary to use special pumping systems or any flow smoothing devices.

Capillary Independence

Unlike some prior art viscometers that require matched capillaries, the present invention does not require matching or balancing the capillaries' restriction in any way. Therefore, the relative viscosity output is independent of the capillaries' restriction tolerance. This makes the viscometer easier to manufacture, as there is no need for capillary trimming or viscometer fluid balance of any kind.

Furthermore, there is no requirement for the relative restriction of the capillaries. They do not have to be equal or scaled in any particular way, although some capillaries' combinations have advantages compared to others. Also, the differential pressure transducers used, do not need to be of the same scale. They can be of different full scale pressure. The only requirement for the capillaries is that the pressure drop across them has to be within the pressure transducers' dynamic range. The pressure drop should not be so large that the transducers saturate, and not so small that the signal-to-noise ratio is unacceptable.

Also, as explained in the detailed description that follows, only one of the capillaries requires special consideration from the chromatographic point of view (internal volume and shear rate). It is the only capillary in which restriction has to be obtained with a particular inside diameter and length to meet the intended internal volume and shear rate. The other capillaries do not require this, so their restriction can be obtained with different inside diameters and lengths. This relaxes even more the design considerations for these capillaries.

Preferred Embodiment

A preferred embodiment of the invention uses three capillaries, two delay volumes, and two differential pressure transducers. These elements are described in detail below.

Concept Description

FIG. 1 shows a diagram of a Three Capillary flow-through Viscometer, wherein it is possible to see the relative location of the three capillaries ($R_1, R_2, R_3$) and the two delay volumes ($D_1, D_2$).

The capillaries are pieces of tubing (normally made of stainless steel), of certain length and inside diameter that create a pressure drop when the solution flows through them. As mentioned above, the pressure drop is given by the Poiseuille's law. In FIG. 1 the capillaries are represented by the saw-tooth waveform, similar to the symbol for an electrical resistance.

The delay volumes are also pieces of tubing, but of much greater inside diameter than that of the capillaries, which creates a negligible pressure drop when the solution flows through them. The purpose of the delay volumes is to delay the arrival of the distribution peak (SEC peak) to the capillary by a time that is proportional to their internal volume, and inversely proportional to the solution flow. They are sized so that the distribution peak is delayed by a time equal to at least the peak width.

The solution flow (Q) is split into two branches. Branch $Q_1$ has two capillaries $R_1, R_3$ with a delay volume $D_1$ located between them, and the other branch $Q_2$ has a delay volume $D_2$ and the other capillary $R_2$ downstream from $D_2$.

Pressures $P_1, P_2$ and $P_3$ are measured across any two of the three capillaries by pressure transducers. However, the third capillary must always be present to get the flow-through capability described above, or the intended viscometer output. The location of the pressure transducers is discussed in detail below.

Initially, a constant solvent flow is passing through both branches $Q_1$, $Q_2$, of the viscometer. Therefore, the three capillaries and the two delay volumes are filled with solvent only (viscosity $\eta_0$). This is the baseline condition.

When a distribution peak (viscosity $\eta$) is introduced into the viscometer, it splits down branches $Q_1$ and $Q_2$ and it enters capillary $R_1$ but not capillary $R_2$ or $R_3$, which remain filled with solvent only (viscosity $\eta_0$) due to the delay volumes. Then, since the viscosity of the distribution peak is different than that of the solvent, the flow restriction of capillary $R_1$ changes, but that of capillaries $R_2$ and $R_3$ do not because they are still filled with solvent. However, the pressure drop across all three capillaries changes because the flow split between the two branches changes, because of the altered flow restrictions. The differential pressure transducers measure two of these pressure drops, and from these measurements it is possible to derive the relative viscosity and the relative flow.

When the distribution peak has passed through $R_1$ entirely and it is inside the delay volumes $D_1$ and $D_2$, there is only solvent (viscosity $\eta_0$) inside all three capillaries, and the viscometer is in the baseline condition again. At this point, the viscometer has delivered completely the relative viscosity chromatogram, which is the analytical part of the whole chromatogram. The remaining part of the relative viscosity chromatogram, the flush part (described below), has no analytical interest.

When the distribution peak (viscosity $\eta$) exits the delay volumes $D_1$ and $D_2$ and enters in $R_2$ and $R_3$, the relative viscosity shows a peak of opposite polarity (normally a negative peak) because $R_1$ is now filled with solvent only (viscosity $\eta$). This peak, however, is broader than the distribution peak due to the bandspreading action of the delay volumes. As mentioned earlier, this part of the chromatogram does not have any analytical interest.

When the distribution peak has gone through $R_2$ and $R_3$ completely, the whole viscometer is filled with solvent only (viscosity $\eta_0$), and the viscometer is back in the baseline condition. At this point, the viscometer is ready to receive a new distribution peak.

As only $R_1$ is in contact with the distribution peak during the analytical part of the chromatogram, it is the only capillary that requires special chromatographic consideration regarding length and inside diameter. $R_1$ has to be selected to create the intended pressure drop, while meeting the internal volume and shear rate chromatographic requirements.

During the analytical part of the chromatogram, $R_2$ and $R_3$ are filled with solvent only, therefore they do not require special chromatographic considerations regarding length and inside diameter. They can be selected to create the intended pressure drop regardless of inside diameter and length.

If the delay volume $D_2$ is eliminated, the viscometer still works but with less than optimal performance. First, the viscometer equations described below would no longer be valid because $R_2$ would be filled with the distribution peak (viscosity $\eta$) during the analytical part of the chromatogram. Even if another set of equations are developed that account for this, the exact viscosity seen by $R_2$ would be different from the viscosity seen by $R_1$, because one of the pressure transducers must always be located before $R_2$ (this is described below). This transducer connection causes bandspreading on the distribution peak that gets to $R_2$, making it impossible to guarantee in $R_2$ a viscosity equal to the viscosity in $R_1$, or even a viscosity easily related to the viscosity in $R_1$. Beside this, $R_2$ would have internal volume requirements, which would mean that the flexibility in length and inside diameter that exist with $D_2$ present, would be lost.

In choosing the size of the delay volumes, they have to be large enough so that the distribution peak does not enter $R_2$ or $R_3$ until the peak has gone through $R_1$ entirely. As described above, once the peak elutes from the delay volumes and enters $R_2$ and $R_3$, the analytical part of the chromatogram is over and the rest of the chromatogram (the flush part) does not have analytical interest. Enough time, however, must elapse between consecutive samples to guarantee that the distribution peak has gone through $R_2$ or $R_3$ entirely before the next sample distribution peak enters $R_1$.

To make the distribution peak elute from both delay volumes at the same time, which is not strictly necessary, they just have to have a volume proportional to the flow through them:

$$\frac{D_1}{D_2} = \frac{Q_1}{Q_2} = \frac{R_2}{R_1 + R_3}$$

For the particular case when $R_2 = R_1 + R_3$, the flow is split in half and both delay volumes can be made equal, which is very convenient but not necessary.

Transducer Flow-through Connections

Figure 2A:
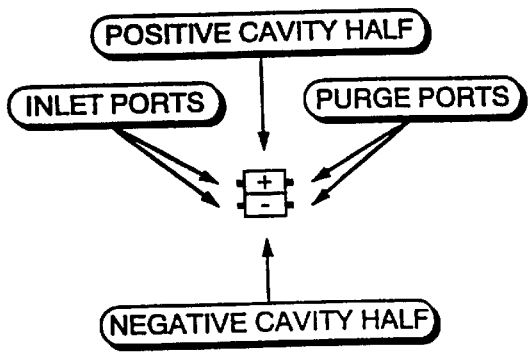
FIG. 2a is a schematic diagram of a differential pressure transducer showing the location of the two transducer cavities, the inlet ports, and the purge ports.

To measure the small pressure drop across the viscometer capillaries, differential pressure transducers are normally used in virtually all viscometer designs. These differential pressure transducers have two cavities of a relatively large volume, separated by a diaphragm. The pressure difference between both cavities deflects the diaphragm, and the diaphragm deflection is converted into an electrical signal by magnetic coupling or well-known other means. One cavity is connected to one end of the capillary, and the other cavity to the other end. Therefore, the transducer electrical signal output is proportional to the pressure drop across the capillary. Each cavity has an inlet port and a purge port. FIG. 2a shows a schematic representation of this type of differential pressure transducer, in which the two transducer halves containing the cavities, are labeled with a "+" and "−" sign. These signs mean that the transducer provides a positive signal if the positive cavity pressure is higher than the negative cavity pressure, and vice versa.

Transducer in "Dead-end" or Standard Connection

Figure 2B:
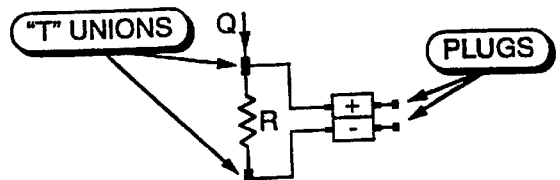
FIG. 2b is a schematic diagram of a differential pressure transducer used in the "dead-end" or standard connection.

FIG. 2b shows a diagram of the transducer used in the standard connection which is not typically used by this invention. The inlet ports connect the cavities to the measuring points (both capillary ends) through pieces of tubing and "T" connections. The purge ports are used to fill the cavities with the solvent used, so there is good pressure transmission between the measuring points and the diaphragm. Once the cavities are filled with solvent, the purge ports are closed, and stay closed until a new purge is required. Therefore, in the standard connection, the transducer cavities are filled with static solvent that just transmits the pressure from the measuring points. Purging, and thus opening of the system, is required to ensure accurate operation of the transducer. The purge operation has to be done from time to time to maintain fresh and bubble free solvent in the cavities, and definitely every time the type of solvent is changed. If the same solvent is kept inside the cavities for a long time, bubbles may form inside, which may cause noise in the pressure signal. If the solvent inside the cavities is different from the solvent passing through the capillary, there is a potential bleeding of the cavity solvent over the capillary solvent stream. This may cause also noise or drift on the signal, along with other physical or chemical problems rated to the solvent mixture. The purge can be done manually, or automatically with solenoid valves or other means. Manual purge presents safety issues due to the hazardous solvents normally used in size exclusion chromatography. Automatic purge presents cost and reliability issues due to the valves and controls required.

Transducer in Flow-through Connection

In the flow-through connection, the transducer purge ports are never closed. Instead, they are used as outlet ports, allowing the solvent to "flow through" the cavities. Both ports in each cavity can be used as either inlet or outlet ports, as long as one is the inlet and the other is the outlet.

Figure 2C:
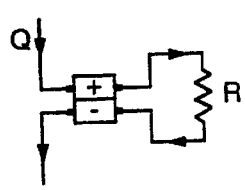
FIG. 2c is a schematic diagram of a differential pressure transducer used in the flow-through connection.

FIG. 2c shows a diagram of the transducer used in the flow-through connection. The flow stream enters one of the transducer cavities through the inlet port. It exits that cavity through the outlet port and goes through the capillary. Then, the flow goes through the other cavity ins similar fashion. There are no dead ends in the flow stream.

The differential pressure measured by the transducer is the same as the pressure measured in the standard connection of FIG. 2b. This is true if the transducer ports or the cavities themselves do not create any significant pressure drop, which is normally true because the inside diameter of the ports and the volume of the cavities are much larger than those of the capillary. If that were not the case, it always is possible to design the transducer to meet this requirement.

This arrangement is a major advantage. In the flow-through connection the transducer purge is not necessary. This eliminates all purge related issues regarding performance, safety, cost and reliability that affect the standard connection. The transducer is always in the optimal performance condition because there are not dead end volumes that bleed other solvent, and the solvent inside the cavities is always as fresh and bubble free as the solvent passing through the capillary. In this regard, it is as if the transducer is permanently being purged. As a purge is not required, there are no safety issues related to solvent handing in manual purge operations. Similarly, valves for automatic purge are not required, eliminating the cost and reliability issues related to the valves.

Transducer in Flow-through Connection, Without Peak Bandspreading

As mentioned above, the flow-through connection of FIG. 2c and the standard connection of FIG. 2b provide the same measured pressure in the transducer. This is true only if solvent viscosity is measured. However, when the viscosity of a distribution peak is measured, the volume of the transducer cavity (positive cavity half) before capillary "R" affects the measurement. The cavity volume is normally large enough to cause bandspreading in the distribution peak. Therefore, the pressure peak measured in the flow-through connection may differ from that measured with the standard connection. However, the volume of the cavity after the capillary (negative cavity half) does not affect the pressure reading. A flow-through connection that overcomes this problem is described below.

Figure 2D:
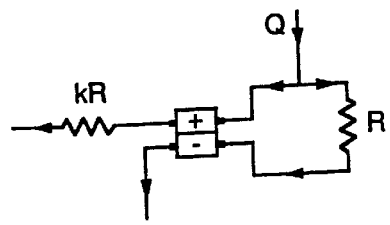
FIG. 2d is a schematic diagram of a differential pressure transducer used in the flow-through connection, without peak bandspreading.

FIG. 2d shows a diagram of the transducer used in the flow-through connection, but without causing peak bandspreading. A portion of the flow is diverted toward another capillary "kR" (normally k>1), and the transducer cavity that causes the peak bandspreading is connected in this new flow path. The pressure measurement is still due only to the flow through "R," but as there is no cavity volume in the flow path before "R" there is no bandspreading in the pressure peak.

However, due to the flow splitting, the pressure measurement is smaller than that obtained with the standard connection, which becomes reduced to k/(k+1). This is not normally a problem, but there is always the possibility to increase the value of both capillaries, or modify the transducer scale, to obtain the same measurement as with the standard connection.

Also, the flow splitting indirectly affects the pressure peak measurement, as the amount of flow split is different while the peak is going through both capillaries. This is fully considered in the invention, which uses this flow-through connection. In any case, this affect can be made very small if k>>1, and a delay volume is inserted before capillary "kR".

It is important to note that in this flow-through connection, the pressure measurement is fully independent of the transducer cavity volume, even if it is very large. This relaxes substantially the transducer mechanical requirements, which basically are reduced to have a low flow-through restriction. FIGS. 6b and 6c show this embodiment.

Flow-through Connections in the Invention

In the invention as depicted in FIG. 1, it is preferred to use the flow-through connection shown in FIG. 2c for capillaries $R_2$ or $R_3$. Due to the delay volumes, these capillaries are filled with solvent (viscosity $\eta_0$) during the analytical part of the chromatogram. Therefore, there is no bandspreading issue to consider in $R_2$ or $R_3$, and the connection of FIG. 2c can be used.

However, this is not the case for capillary $R_1$ (FIG. 1), because it is filled with the distribution peak (viscosity $\eta$), during the analytical part of the chromatogram. The bandspreading issue arises if the connection type of FIG. 2c is used for capillary Therefore, for capillary $R_1$ it is necessary to use the connection of FIG. 2d, as explained below.

The transducer connections for measuring $P_1$ across capillary $R_1$ (FIG. 1) may be made in several locations with identical results. The pressure before $R_1$ (in the $Q_1$ branch) is the same as the pressure before delay volume $D_2$ (in the $Q_2$ branch). Since $D_2$ does not cause any flow restriction, or it is negligible compared with the capillaries' restriction, the pressure before $R_1$ is also the same as the pressure "after" $D_2$. Therefore, the positive cavity of the transducer to measure $P_1$ can be connected at either side of $D_2$. In both cases, the connection type is shown in FIG. 2d, and it does not cause any bandspreading in the distribution peak going through $R_1$. Similarly, the negative cavity of the transducer to measure $P_1$ can be connected at either side of $D_1$.

FIGS. 3a through 3d show the four possible ways to measure the pressure across capillary $R_1$ ($P_1$) with the transducer connected flow-through and without causing any bandspreading in the distribution peak going through $R_1$.

Figure 3A:
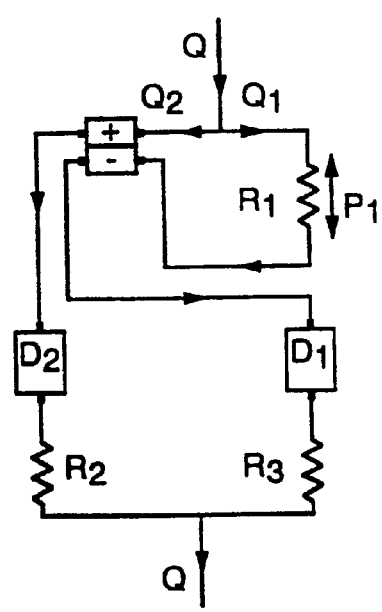
FIGS. 3a through 3d are schematic diagrams of four possible ways to measure the pressure across capillary $R_1$ ($P_1$) with the transducer connected flow-through and without causing any bandspreading in the distribution peak going through $R_1$.
Figure 3B:
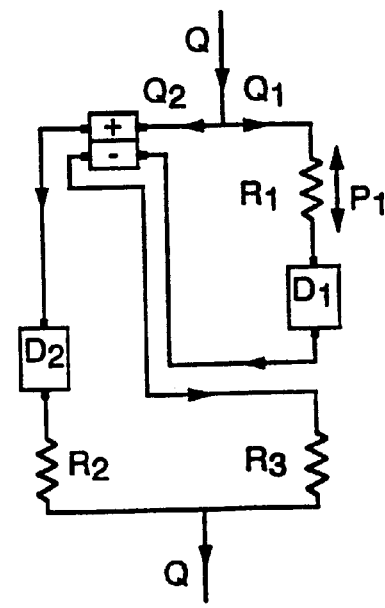
Figure 3C:
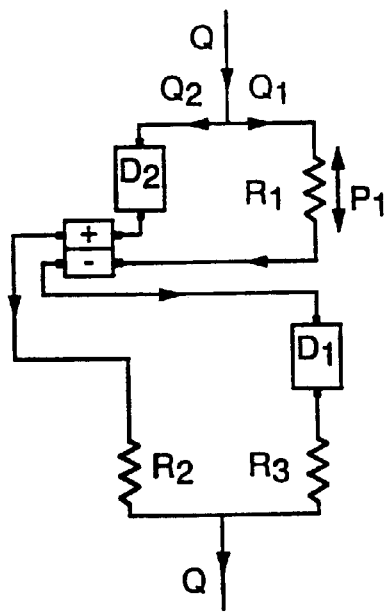
Figure 3D:
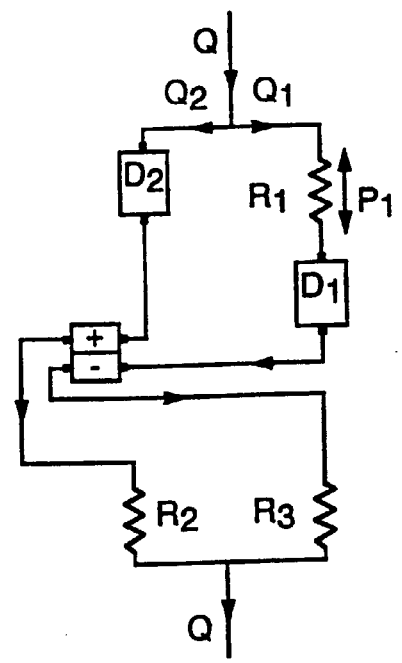

The preferred connections to measure $P_1$ flow-through are those of FIG. 3a and FIG. 3d. This is because if the delay volumes' flow restriction is not negligible, it will slightly affect $P_1$ in all cases except in the connection of FIG. 3a. For connection type 3d, if the delay volumes' restriction is proportional to their respective flows, the effect of both delay volumes is canceled in the connection of FIG. 3d.

Figure 4E:
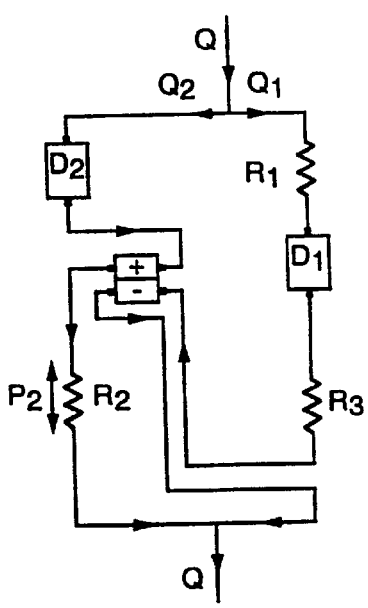
Figure 4F:
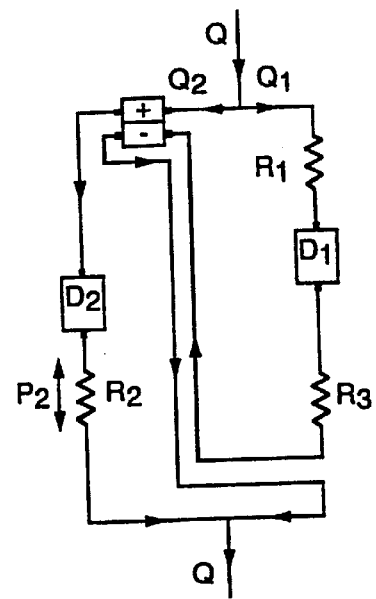

FIGS. 4a through 4f show the six possible ways to configure the transducer connections to measure the pressure across $R_2$ ($P_2$) with the transducer connected flow-through and without causing any bandspreading in the distribution peak going through $R_1$. FIG. 4a shows the preferred connection (as in FIG. 2c), and the others are other embodiments based on ways to connect the transducer cavities at different points with the same pressure.

Figure 5A:
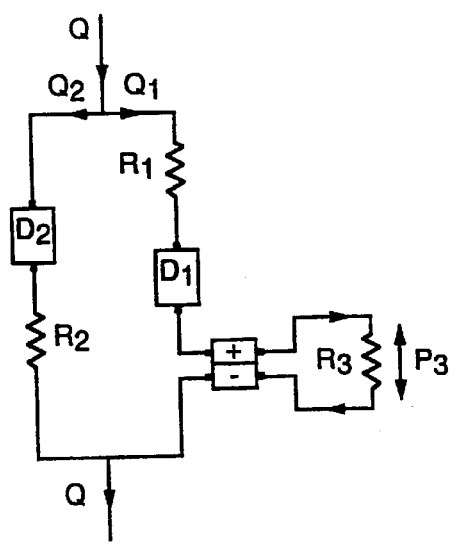
FIGS. 5a through 5f are schematic diagrams of six possible ways to measure the pressure across $R_3(P_3)$ with the transducer connected flow-through and without causing any bandspreading in the distribution peak going through $R_1$.
Figure 5B:
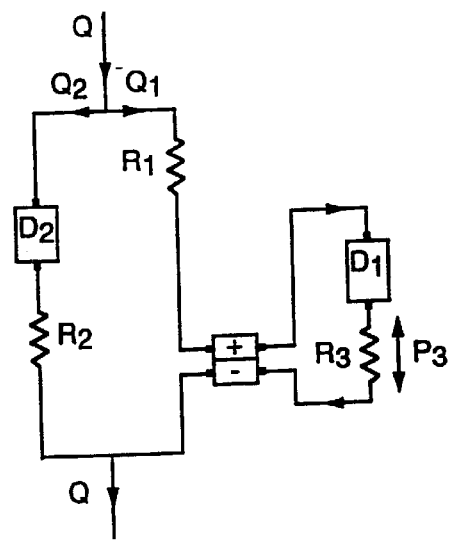
Figure 5C:
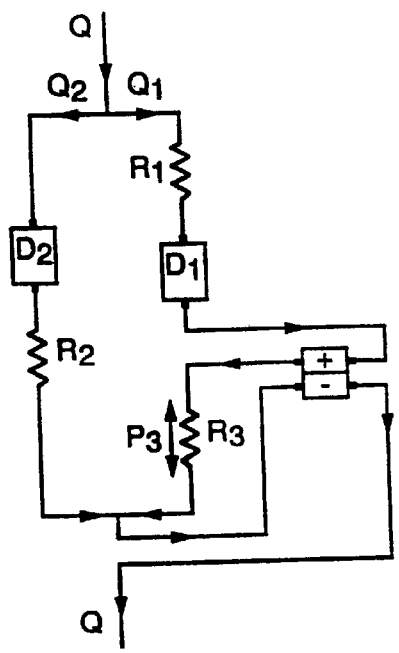
Figure 5D:
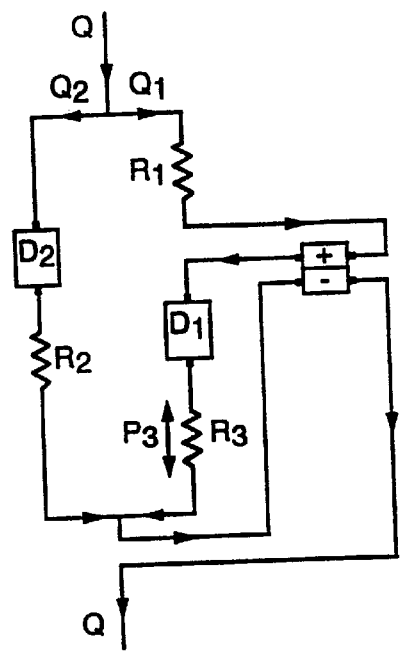
Figure 5E:
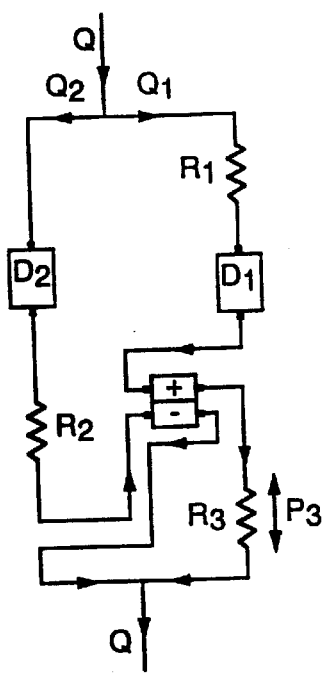
Figure 5F:
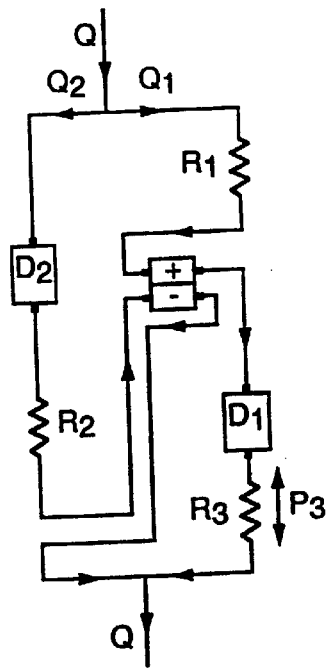

FIGS. 5a through 5f show the six possible ways to configure the transducer connections to measure the pressure across $R_3$ ($P_3$) with the transducer connected flow-through and without causing any bandspreading in the distribution peak going through $R_1$. FIG. 5a shows the preferred connection (as in FIG. 2c), and the others are other embodiments based on ways to connect the transducer cavities at different points with the same pressure.

The present invention requires any two of these three pressure measurements. Combining all possible ways to measure $P_1$, $P_2$ and $P_3$ described above, results in several possible flow-through connections of the two transducers used. If $P_1$ and $P_2$ are the pressure measurements chosen, there are a total of 24 transducer flow-through connection combinations from FIGS. 3 and 4. Also, 12 of these 24 combinations have one cavity of each transducer connected at the same point. This creates another 12 distinct combinations by differentiating which transducer cavity is connected first. Therefore, there are a total of 36 transducer flow-through combinations using $P_1$ and $P_2$.

If $P_1$ and $P_3$ are the pressure measurements chosen, there is a total of 24 transducer flow-through connection combinations from FIGS. 3 and 5. Also, 12 of these 24 combinations have one cavity of each transducer connected at the same point. This creates another 12 distinct combinations by differentiating which transducer cavity is connected first. Therefore, there are a total of 36 transducer flow-through combinations using $P_1$ and $P_3$.

If $P_2$ and $P_3$ are the pressure measurements chosen, there are a total of 36 transducer flow-through connection combinations from FIGS. 4 and 5. Also, 12 of these 36 combinations have one cavity of each transducer connected at the same point. This creates another 12 distinct combinations by differentiating which transducer cavity is connected first. Therefore, there are a total of 48 transducer flow-through combinations using $P_2$ and $P_3$.

Figure 7A:
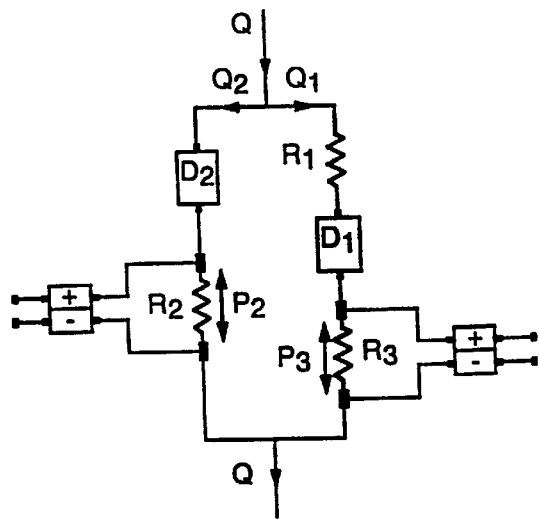
FIGS. 7a through 7c are schematic diagrams of the three embodiment examples of FIGS. 6a through 6c, but showing the transducers in "dead-end" or standard connection.
Figure 7B:
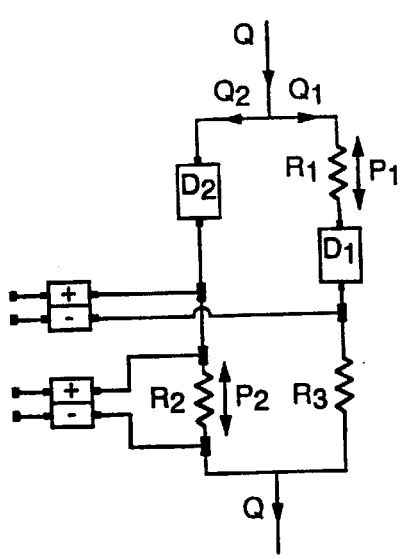
Figure 7C:
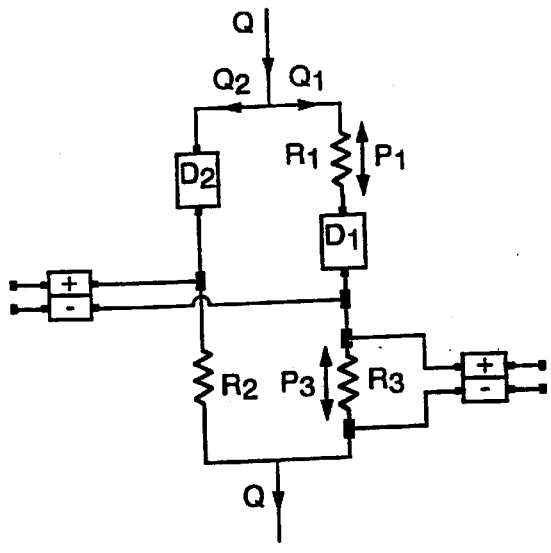

As a result of these combinations, there are a total of 120 possible distinct embodiments of the invention. All of them provide flow-through Relative Viscosity measurements, without causing any bandspreading in the distribution peak. FIGS. 6a through 6c show schematic diagrams of three distinct embodiments or examples. FIGS. 7a through 7c show the same three embodiments, using the transducers in "dead-end" or standard connection.

Preferred Embodiment

Figure 8:
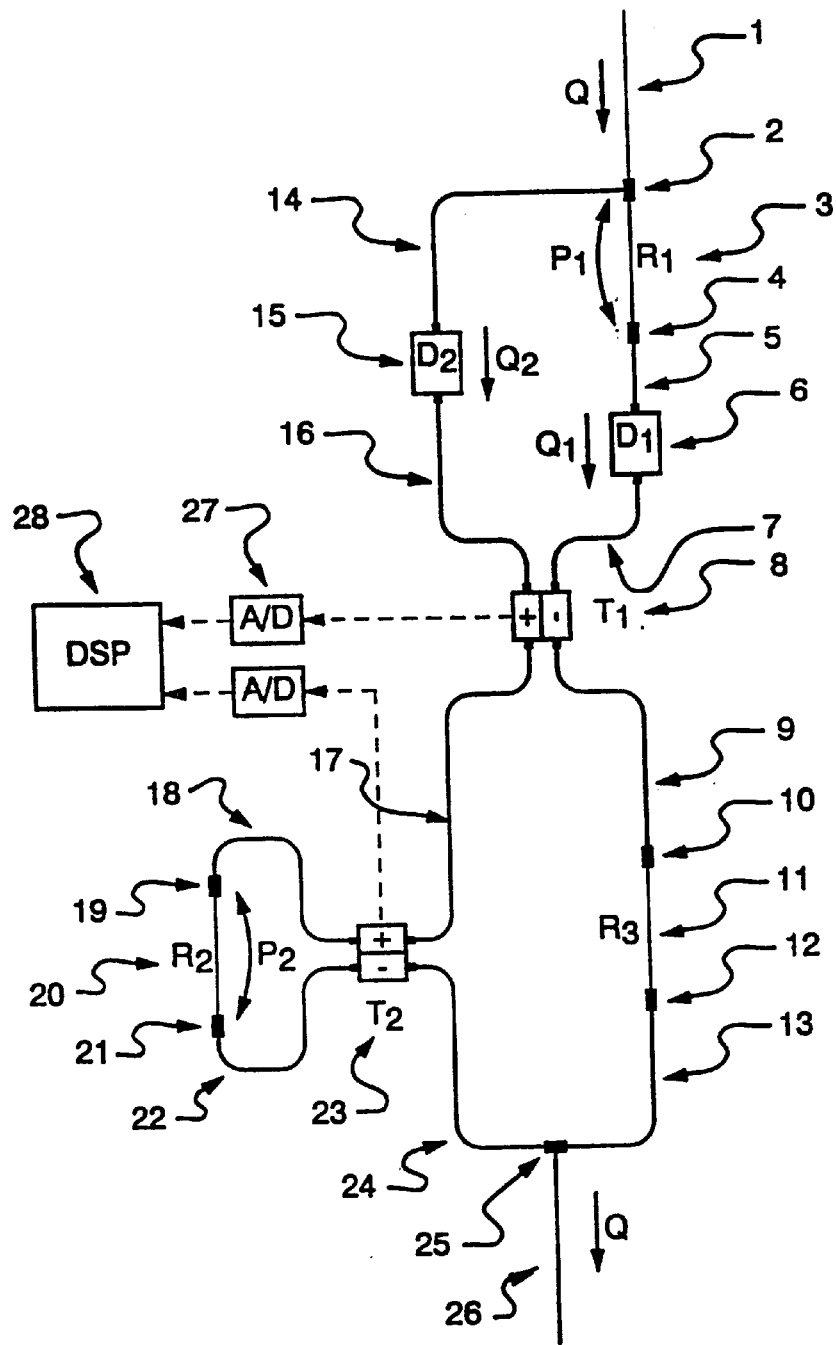
FIG. 8 is a schematic diagram of the preferred embodiment of the Invention.

FIG. 8 shows the preferred embodiment of the invention. The main design consideration for the practical implementation of the invention is that only the three capillaries cause a significant flow restriction. All other elements used in the design must create a pressure drop that is negligible compared to that of the capillaries. The following description refers to numbered elements in that Figs.

The solution flow (Q) arrives at the viscometer through small inside diameter tubing (1) to minimize peak bandspreading. The flow is split into two components, $Q_1$ and $Q_2$, at the low internal volume "T" union (2).

The $Q_1$ flow goes through the following elements: Capillary $R_1$ (3) where a pressure drop $P_1$ is developed; a large inside diameter union (4); a large inside diameter connecting tubing (5); delay volume $D_1$ (6); a large inside diameter connecting tubing (7); the negative cavity of transducer $T_1$ (8); a large inside diameter connecting tubing (9); a large inside diameter union (10); capillary $R_3$ (11); a large inside diameter union (12); and a large inside diameter connecting tubing (13).

The $Q_2$ flow goes through the following elements: A large inside diameter connecting tubing (14); delay volume $D_2$ (15); a large inside diameter connecting tubing (16); the positive cavity of transducer $T_1$ (8); a large inside diameter connecting tubing (17); the positive cavity of transducer $T_2$ (23); a large inside diameter connecting tubing (18); a large inside diameter union (19); capillary $R_2$ (20) where a pressure drop $P_2$ is developed; a large inside diameter union (21); a large inside diameter connecting tubing (22); the negative cavity of transducer $T_2$ (23); and a large inside diameter connecting tubing (24).

The two flow components, $Q_1$ and $Q_2$, are recombined at the large inside diameter "T" union (25), and then the total flow Q exits the viscometer through tubing (26). The pressure drop caused by tubing (26) or any other element connected after the viscometer does not affect the viscometer performance as long as the maximum absolute pressure of the transducers is not exceeded. Also, "T" union (25) and exit tubing (26) are not necessary if both flow branches are vented to the atmosphere.

The electrical outputs of transducer $T_1$ (8) and transducer $T_2$ (23), are sent to analog to digital converters (27). The digital outputs from the converters are processed in a digital signal processor (28), where the relative viscosity and relative flow information is obtained.

The capillaries are made of a piece of stainless steel tubing with inside diameter normally in the range from 0.009" to 0.014". A preferred size is 0.012". Other materials such as aluminum or engineered plastics are also possible. The large inside diameter connecting tubing and unions have normally an inside diameter of 0.040" or larger. The delay volumes are normally made with a piece of tubing with inside diameter of 0.062" or larger.

Capillary $R_1$ is the only capillary that contacts the distribution peak during the analytical part of the chromatogram. Therefore, it is the only capillary that requires special chromatographic consideration regarding length and inside diameter. $R_1$ is selected to create the intended pressure drop which is within the dynamic range of the transducer, while meeting the internal volume (typically 8–16 $\mu$l) and fluid shear rate (typically 3000–4000 sec.$^{-1}$) chromatographic requirements. Conversely, $R_2$ and $R_3$ do not require special chromatographic considerations regarding length and inside diameter, because they are solvent filled during the analytical part of the chromatogram. They can be selected to create the intended pressure drop regardless of inside diameter and length.

The flow path of a distribution peak as in SEC through the invention is as follows. Initially, a constant solvent flow ($Q_0$) is passing through the viscometer. Therefore, all viscometer elements are filled with solvent only (viscosity $\eta_0$). This is the baseline condition, in which the transducers are reading baseline pressures $P_{1Baseline}$ and $P_{2Baseline}$.

The solution flow (Q) containing a distribution peak (viscosity $\eta$) arrives at the viscometer through tubing (1). In the "T" union (2) the peak is split into two parts (not necessarily equal), so that part of the peak goes to capillary $R_1$ (3), and part to delay volume $D_2$ (15) through tubing (14).

This causes two effects: the pressure drop across capillary $R_1$ (3) increases (assuming $\eta > \eta_0$) due to the higher viscosity solution going through the capillary, and because of this, the flow split ratio changes with respect to the flow split in the baseline condition.

The portion of the peak going through $Q_2$ (15) takes some time to elute from this delay volume. During this time, the $Q_1$ portion of the peak passes through capillary $R_1$ (3), and enters delay volume $D_1$ (6) through union (4) and tubing (5). Similarly, this portion of the peak takes some time to exit delay volume $D_1$ (6).

While the peak (viscosity $\eta$) passes through capillary $R_1$ (3) and is delayed by delay volumes $D_1$ (6) and $D_2$ (15), the rest of the viscometer elements are still filled with solvent (viscosity $\eta_0$). Therefore, the pressure drop change measured by transducer $T_2$ (23), with respect to the pressure measured during the Baseline condition, is directly related to the flow split change. However, the pressure drop change measured by transducer $T_1$ (8), with respect to the pressure measured during the Baseline condition, is related to both the viscosity change and the flow split change. From the two pressure measurements it is possible to extract the relative viscosity information, as discussed below in the signal processing sections.

Once the peak has gone through $R_1$ (3) entirely, and it is inside the delay volumes $D_1$ (6) and $D_1$ (15), the "analytical" part of the chromatogram has finished, and all relevant relative viscosity information has already been acquired. The rest of the viscometer elements, now including $R_1$ (3) also, are filled with solvent (viscosity $\eta_0$). In this situation the viscometer is in the Baseline condition. The peak then exits the delay volumes $D_1$ (6) and $D_2$ (15), starting the "flush" part of the chromatogram. The peak may exit simultaneously or at different times from both delay volumes, depending on their size and the flow split, but this is unimportant as this part of the chromatogram does not have any analytical interest.

The peak elutes from delay volume $D_1$ (6) broader than originally, goes through tubing (7) and the negative cavity of transducer $T_1$ (8). Then it enters in capillary $R_3$ (11) through tubing (9) and union (10). This causes a flow split change that is measured as a pressure drop change by both transducers $T_1$ (8) and $T_2$ (23). The peak then goes through union (12), tubing (13), the "T" union (25) where the flow from both branches is recombined, and the exit tubing (26).

The peak elutes from delay volume $D_2$ (15) broader than originally, goes through tubing (16), the positive cavity of transducer $T_1$ (8), tubing (17) and the positive cavity of transducer $T_2$ (23). Then it enters in capillary $R_2$ (20) through tubing (18) and union (19). The viscosity change in $R_2$ (20) is measured by transducer $T_2$ (23) as a pressure drop change. Also, this causes a flow split change that is measured as a pressure drop change by both transducers $T_1$ (8) and $T_2$ (23). The peak then goes through union (21), tubing (22), the negative cavity of transducer $T_2$ (23), tubing (24), the "T" union (25) where the flow from both branches is recombined, and the exit tubing (26).

The combined effect of the peak (viscosity $\eta$) going through capillaries $R_2$ (20) and $R_3$ (11), while just solvent (viscosity $\eta_0$) is passing through capillary $R_1$ (3), is that the relative viscosity shows a peak of opposite polarity (normally a negative peak) than that of the relative viscosity analytical peak (normally a positive peak). The negative peak, however, is broader than the analytical peak due to the bandspreading and diffusion effect of the delay volumes.

Once the peak has gone through capillaries $R_2$ and $R_3$ completely, the whole viscometer is again filled with solvent only (viscosity $\eta_0$). This leaves the viscometer back in the baseline condition, ready to receive a new distribution peak.

Signal Processing

A. Transducers' Signal Preprocessing

Two properties of the viscometer pressure transducers are mainly responsible for the sensitivity of multicapillary viscometers to fast flow changes. One is the slight non-linearity in the transducers' response and the other is their dynamic response.

In some cases, the pressure transducers' signals do not follow exactly the Poiseuille's law, so the relationship between the measured pressures and the viscometer flow is slightly non-linear. The pressure transducers themselves are responsible for most of this non-linearity, although other elements also can contribute, such as capillaries that are curved due to space constraints of the practical viscometer construction.

The small non-linearity in the transducers' response normally does not affect the low frequency response of the multi-capillary viscometers, because the pressure changes normally involved are very small compared with the full scale transducers. However, if significant flow fluctuations are present, whether slow or fast, they are slightly distorted by the non-linear response. Consequently, the viscometer's normal signal processing of transducer signals is unable to cancel the flow disturbance.

Actually, the difference in transducers' non-linearities determines the magnitude of this effect. If the non-linearities of the transducers' responses were exactly equal, then the viscometer processing of transducers' signals would cancel the flow disturbances completely.

The other property of viscometer pressure transducers mentioned previously is the dynamic response of the pressure transducers. As with non-linearities, it is the difference in transducers' dynamic responses that affects the sensitivity of multi-capillary viscometers to fast flow changes.

Due to several factors, the dynamic response to fast flow changes of the transducers' used in a multicapillary viscometer design is different for each transducer. This makes the "shape" of the measured pressure transients different in every transducer. The main factors responsible for this behavior are the differing locations of the transducers in the viscometer fluid arrangement, the mechanical and fluid capacitance of each transducer's diaphragm, and the fluid capacitance of delay volumes used in the design.

The digital signal preprocessing method disclosed in this invention consists substantially of two steps, addressing issues of non-linearity and dynamic response in multicapillary systems as discussed hereinbefore. This method is independent of the type of multi-capillary viscometer design, so it can be applied to any viscometer with two or more capillaries and at least two pressure transducers. The result is a significant performance increase in viscometer rejection to high frequency flow disturbances, without affecting the viscometer dynamic response.

The two method steps are referred to as "Pressure Linearization" and Dynamic Equalization" below, and they are normally performed in this order. They can, however, be performed in reverse order, such that the Dynamic Equalization is done first, and the Pressure Linearization second, but the performance increase in viscometer rejection to high frequency flow disturbances may not be as good as with the steps in the normal order.

Figure 15:
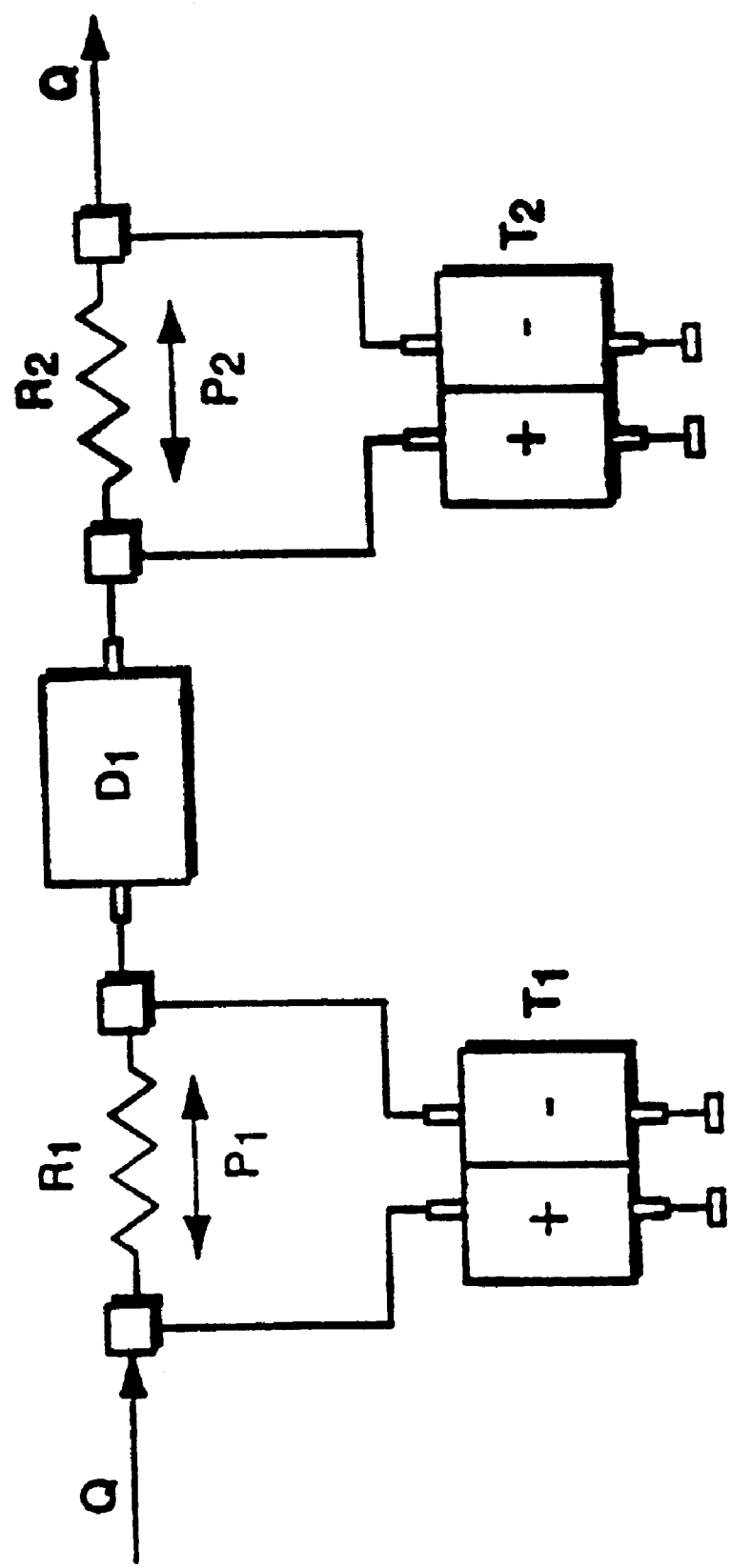
FIG. 15 is a schematic diagram of a dual capillary, dual transducer viscometer.

FIGS. 15 and 6b show schematic diagrams of two multicapillary viscometer designs that could benefit from the method of the present invention. FIG. 15 shows a Dual capillary, dual transducer viscometer, and FIG. 6b shows a Triple Capillary, dual transducer viscometer.

Once the pressure signals have been "preprocessed" using the method of the present invention, they are further processed using the normal processing corresponding to the particular type of viscometer design. In the present example, such a processing method is given in Part B, Transducers Signal Processing, which follows this section.

It is important to mention that the same results obtained using the digital signal processing method disclosed herein also can be obtained using analog electronics at the pressure transducer outputs. This solution, although possible, is harder to implement and it is normally less flexible to accommodate changing viscometer conditions.

The two method steps are described below for the particular case of a dual pressure transducer viscometer design. The same concepts can be applied to other viscometer designs with more than two pressure measurements. In the following description, P1 and P2 are referred to as the pressure signals coming from both transducers.

1.) Pressure Linearization

By way of introduction which is more specifically set out below, using a quadratic fit, each pressure transducer signal is linearized with respect to flow. This compensates for any small non-linearity that the pressure to flow relationships may have, and increases the Relative Viscosity independence of viscometer flow changes.

The basic idea of this correction is to use, for each pressure signal, a curve fit of the pressure to flow relationship, to calculate pressure values that are linearly related to flow around the baseline flow.

The following example uses a quadratic fit. For each transducer, pressure measurements at two known flows are taken, which are used to calculate the coefficients of the quadratic fit. While these pressure measurements are taken, the viscometer must be filled, with solvent only; therefore, there should not be any traces of old solvent or samples inside the viscometer.

One of the pressure measurements ($P1_{Baseline}$ and $P2_{Baseline}$) is taken at the baseline flow ($Flow_{Baseline}$) the viscometer will have during normal operation. The other pressure measurement ($P_{1Mid}$ and $P_{2Mid}$), is taken at a mid-flow point ($Flow_{Mid}$) near the baseline flow. If pump pulsation appears on the pressure signals, special care has to be considered while taking these pressure measurements. In order that the pump pulsation does not affect the measurements, they have to be calculated as the average of instantaneous pressure readings during an integer number of pump pulse cycles. The coefficients to use in the quadratic fit are given by:

$$k_1 = \frac{P1_{Mid} - P1_{Baseline} \frac{Flow_{Mid}}{Flow_{Baseline}}}{P1_{Mid} \cdot (P1_{Baseline} - P1_{Mid})}$$

$$k_2 = \frac{P2_{Mid} - P2_{Baseline} \frac{Flow_{Mid}}{Flow_{Baseline}}}{P2_{Mid} \cdot (P2_{Baseline} - P2_{Mid})}$$

$$k_1 = \frac{P1_{Mid} - P1_{Baseline} \frac{Flow_{Mid}}{Flow_{Baseline}} - P1_{mid}^2}{P1_{Mid} \cdot (P1_{Baseline} - P1_{Mid})}$$

$$k_1 = \frac{P1_{Mid} - P1_{Baseline} \frac{Flow_{Mid}}{Flow_{Baseline}} - P2_{mid}^2}{P2_{Mid} \cdot (P2_{Baseline} - P2_{Mid})}$$

With these coefficients, the linearized pressures ($P1_{lin}$ and $P2_{lin}$) are calculated as a function of the subsequent measured pressures (P1 and P2) using the following equations:

$P1_{lin} = k_1 \cdot P1^2 + m_1 \cdot P1$ $P2_{lin} = k_2 \cdot P2^2 + m_2 \cdot P2$ These linearized pressure values are the ones used in the following steps.

2.) Dynamic Equalization

The purpose of this step is to equalize the dynamic response of both pressure signals. This makes the Relative Viscosity signal independent of high frequency flow components like the pulses from the pumping system, or the fast transients from the sample injector system.

Due to the filtering effect created by the different fluidic elements in the viscometer, as well as by the pressure transducers themselves, the flow transients through the viscometer appear as filtered transients in the pressure transducer outputs. As this filtering effect is different for each pressure signal, the filtered pressure transients also are different.

The result of this different dynamic behavior is that the flow transients in one of the pressure signals (eg. P1) appear "smoothed" compared to the same flow transients in another pressure signal (eg. P2), and this smoothing is only due to the viscometer fluidics. A study of the viscometer fluidics geometry would normally show which pressure signal will have the smoothed pressure transients. In the description that follows, it is assumed that P1 is the smoothed pressure signal. The "Dynamic Equalization" applies to the P2 pressure signal the same smoothing that the viscometer fluidics applies to the P1 pressure signal. The "Dynamic Equalization" does not alter the P1 pressure signal in any way. The end result is that both pressure signals respond equally to flow transients, and therefore, that these transients are canceled out either when the Relative Viscosity signal is calculated or during the normal pressure signal processing corresponding to the particular type of multicapillary viscometer design.

It is important to note that the Dynamic Equalization does not modify in any way the steady state response of the viscometer, which solely depends on the signal processing corresponding to the viscometer design, such as the Relative Viscosity calculation described in the next step.

The "Dynamic Equalization" funds out what is the transfer function that makes the P1 pressure signal appear smoothed compared to the P2 pressure signal, and then applies this transfer function to the P2 pressure signal. This is a task easy to implement in a sampled data system, although other methods could be used.

A basic model of most multicapillary viscometer designs, reveals that this transfer function has a pole zero pair in the Laplace transform plane. This translates to a function in the discrete time domain in which the present output of the transfer function, depends on the present input, and on the previous input and output of a sampled data system, according to the following equation:

Output($t$)=A·Output($t-1$)+B·Input($t$)+C·Input($t-1$)

Where A, B and C are weighting coefficients, "t" represents the present sample, and "t–1" represent the previous sample. The condition to satisfy so that this transfer function does not alter the steady state, is that the sum of the three coefficients must be unity. Once the three coefficients are known, the "equalized" P2 pressure signal ($P2_{eqzd}(t)$) is obtained from the linearized P2 pressure signal ($P2_{lin}(t)$) with this equation:

$P2_{eqzd}(t) = A \cdot P2_{eqzd}(t-1) + B \cdot P2_{lin}(t) + C \cdot P2_{lin}(t-1) \quad A+B+C=1$ It is possible to use more coefficients and "t–2", "t–3" . . . "t–n" samples to obtain a more precise representation of the transfer function. The procedure to follow would be the same described below, but three coefficients are normally adequate. The calculation of coefficients A B and C is a multiple step process based on arrays of pressure data points collected during baseline flow. Another possible method to calculate the coefficients from real data would be using a learning neural network, and those skilled in the art would find other methods as well.

2.1) Pressure Arrays

Arrays of linearized P1 and linearized P2 data points are collected with the viscometer filled with solvent only, and at the "Baseline flow" the viscometer will have during normal operation. The arrays should be long enough to include at least one flow transient. If there are pump pulses, including few pulses in the arrays is sufficient. If there are no pump pulses, they can be artificially generated by changing the flow slightly at known times. The purpose of this is to capture the response of both pressure transducers to the same flow transients, from which the coefficients can be calculated.

It is essential for this calculation that the two arrays be filled with pressure samples collected substantially simultaneously (each element in both arrays corresponds to samples taken at the same time).

In the description that follows, the variable "t" refers to one particular element of the arrays, the variable "t−1" refers to one element before element "t", and the variable "t−2" refers to two elements before element "t". It is assumed that the sampling rate at which the data points were collected, is the same sampling rate that will be used during normal data acquisition. It is also assumed that the increasing order of the elements means increasing time when the elements were collected. The arrays are named "ArrayP1" and "ArrayP2", each containing elements "$P1_{lin}(t)$" and "$P2_{lin}(t)$" respectively.

2.2) Normalization

In this step, the two arrays are normalized to unity, to eliminate the steady state component of the pressure data points, leaving the variable component only. Following the same procedure described in the "Pressure linearization" step, data points averages are calculated to obtain baseline pressure values ($P1_{Baseline}$ and $P2_{Baseline}$) for each array. Then each pressure data point in the arrays is divided by their respective baseline pressure value. The normalized arrays become "ArrayN1" and "ArrayN2", each containing elements "N1(t)" and "N2(t)" respectively.

$$N1(t) = \frac{P1_{lin}(t)}{P1_{Baseline}}$$

$$N2(t) = \frac{P2_{lin}(t)}{P2_{Baseline}}$$

2.3) Filter

The noise present in the pressure signals affects severely the calculation of coefficients B and C therefore the signals in the normalized arrays are filtered with a single pole filter to improve this. The filtered arrays become "ArrayF1" and "ArrayF2", each containing elements "F1(t)" and "F2(t)" respectively.

$$F1(t)=0.8 \cdot F1(t-1)+0.2 \cdot N1(t)$$

$$F2(t)=0.8 \cdot F2(t-1)+0.2 \cdot N2(t)$$

The coefficients in the equations above represent a particular amount of filtering for a particular sampling rate. The value of the two coefficients in each case depends on the sampling rate used and the amount of noise present in the pressure signals, but their sum has to be always unity.

2.4) Calculation of "ArrayA" and "ArrayB"

As the two filtered arrays do not have a steady state component, their respective elements are related with the same "Dynamic Equalization" equation described above. That is, the equation that provides $P2_{eqzd}(t)$ values from $P2_{lin}$ values, should be the same equation that provides F1(t) values from F2(t) values. Therefore, F1(t) and F1(t−1) can be expressed as follows:

$$F1(t)=A \cdot F1(t-1)+B \cdot F2(t)+C \cdot F2(t-1) F1(t-1)=A \cdot F1(t-2)+B \cdot F2(t-1)+C \cdot F2(t-2) A+B+C=1$$

From these equations it is possible to express A and B as a function of F1 and F2 values only:

$$A = \frac{(F2(t-2) - F2(t-1)) \cdot F1(t) + (F2(t) - F2(t-1)) \cdot F1(t-1) - F2(t-2) \cdot F2(t) + F2(t-1)^2}{(F2(t-2) - F2(t-1)) \cdot F1(t-1) + (F2(t) - F2(t-1)) \cdot F1(t-2) - F2(t-2) \cdot F2(t) + F2(t-1)^2}$$

$$B = \frac{(F1(t-1) - F1(t-2)) \cdot F2(t-1) + (F1(t-1) - F1(t)) \cdot F2(t-2) + F1(t-2) \cdot F1(t) - F1(t-1)^2}{(F2(t-2) - F2(t-1)) \cdot F1(t-1) + (F2(t) - F2(t-1)) \cdot F1(t-2) - F2(t-2) \cdot F2(t) + F2(t-1)^2}$$

Applying these equations to all the elements of "ArrayF1" and "ArrayF2", it is possible to obtain a collection of values of A and values of B, that is, "ArrayA" and "ArrayB".

2.5) Calculation of Coefficients A and B

In an ideal and perfect system, the elements in "ArrayA" should all be the same, and the elements in "ArrayB" should all be the same also. However, this is not the case in a real system due to the noise present in the pressure signals. The elements in the arrays are different, although there is a clear tendency towards a particular value, which is the value of the coefficient to find. Therefore, the value of coefficient A is the value with highest probability of occurrence among the elements of "ArrayA". The same applies to "ArrayB".

Before performing this step, some elements in both arrays that have unreasonable values are discarded. Both coefficient A and coefficient B have limits imposed by the model used to represent the dynamic behavior of the viscometer, and by the sampling rate used. Normally these coefficients should be positive and not greater than one, although for a particular viscometer arrangement and sampling rate, narrower boundaries can be calculated. All elements in the arrays with values beyond the limits are due to noise in the system and have to be discarded.

One method for easy computation of the value with highest probability of occurrence among the rest of elements in the arrays is explained below, although other methods may work as well.

To calculate coefficient A, the mean and the median of the elements in "ArrayA" are calculated. Then, if the mean is higher than the median, all elements with values higher than the mean are discarded. If the mean is lower than the median, all elements with values lower than the mean are discarded. A new mean and median values are calculated, and more array elements are discarded following the same procedure. This process is repeated until the mean is equal to the median, which normally happens when there are only two elements left in the array. Coefficient A is the value obtained for that equal mean and median. The same procedure is followed to calculate coefficient B from "ArrayB".

2.6) Calculation of Coefficient C

Once the value of coefficients A and B are known, coefficient C can be calculated from the requirement that the sum of the three coefficients must be unity.

Therefore:

$$C = 1 - A - B$$

B. Transducers' signal processing

In this step, the basic Relative Viscosity and Relative Flow calculations are performed using the preprocessed pressure signals derived above.

Considering the diagram of FIG. 1, where:

$$R_1 = \frac{8}{\pi} \cdot \frac{L_1}{r_1^4}$$

$$R_2 = \frac{8}{\pi} \cdot \frac{L_2}{r_2^4}$$

$$R_3 = \frac{8}{\pi} \cdot \frac{L_3}{r_3^4}$$

According to Poiseuille's law, the pressure drop across the capillaries is given by:

$$P_1 = R_1 \cdot \eta \cdot Q_1 \qquad P_2 = R_2 \cdot \eta_0 \cdot Q_2 \qquad P_3 = R_3 \cdot \eta_0 \cdot Q_1$$

Also, the relationship between the flow in the two branches is:

$$Q_1 + Q_2 = Q$$

$$\frac{Q_1}{Q_2} = \frac{R_2 \cdot \eta_0}{R_1 \cdot \eta + R_3 \cdot \eta_0}$$

With these equations it is possible to obtain the following expressions dependent on flow "Q":

$$P_1 = Q \cdot R_1 \cdot R_2 \cdot \frac{\eta}{\left(R_1 \frac{\eta}{\eta_0} + R_2 + R_3\right)}$$

$$P_2 = Q \cdot R_2 \cdot \frac{R_1 \cdot \eta + R_3 \cdot \eta_0}{\left(R_1 \frac{\eta}{\eta_0} + R_2 + R_3\right)}$$

$$P_3 = Q \cdot R_3 \cdot R_2 \cdot \frac{\eta_0}{R_1 \frac{\eta}{\eta_0} + R_2 + R_3}$$

When the viscometer is filled with solvent only ($\eta = \eta_0$), and there is a reference baseline flow $Q_0$ through the viscometer, the expressions become:

$$P1_{Baseline} = Q_0 \cdot R_1 \cdot R_2 \cdot \frac{\eta_0}{(R_1 + R_2 + R_3)}$$

$$P2_{Baseline} = Q_0 \cdot R_2 \cdot (R_1 + R_3) \frac{\eta_0}{(R_1 + R_2 + R_3)}$$

$$P3_{Baseline} = Q_0 \cdot R_3 \cdot R_2 \cdot \frac{\eta_0}{(R_1 + R_2 + R_3)}$$

For the preferred embodiment of FIG. 8, the two transducers that are used measure the pressure drop across capillaries $R_1$ and $R_2$ only. Therefore, only the equations of $P_1$, $P_2$, $P1_{Baseline}$, and $P2_{baseline}$ are considered.

Operating with these four equations, it is possible to derive expressions for the Relative Viscosity and the Relative Flow:

$$\eta_{rel} = \frac{\eta}{\eta_0} = \frac{P_1 \cdot (P2_{Baseline} - P1_{Baseline})}{P1_{Baseline} \cdot (P_2 - P_1)}$$

$$Q_{rel} = \frac{Q}{Q_0} =$$

$$\frac{P_2 - P_1}{P2_{Baseline}\left(2 - \frac{P_1}{P_2}\right) - P1_{Baseline}} \cdot \left(\frac{R_1 \cdot \eta_{rel} + R_2 + R_3}{R_1 + R_2 + R_3}\right) \cdot \left(1 + \frac{R_1 + R_3}{R_1 \cdot \eta_{rel} + R_3}\right)$$

If delay volume D2 is removed, the pressure drop across the capillaries becomes:

$$P_1 = R_1 \cdot \eta \cdot Q_1$$

$$P_2 = R_2 \cdot \eta \cdot Q_2$$

$$P_3 = R_3 \cdot \eta \cdot Q_1$$

Using the same procedure as described above, it is possible to obtain the Relative Viscosity and the Relative How expression when $D_2$ is not present:

$$\eta_{rel} = \frac{\eta}{\eta_0} = \frac{P_1 \cdot (P2_{Baseline} - P1_{Baseline})}{P1_{Baseline} \cdot (P_2 - P_1)}$$

$$Q_{rel} = \frac{Q}{Q_0} =$$

$$\frac{P_2 - P_1}{P2_{Baseline}\left(2 - \frac{P_1}{P_2}\right) - P1_{Baseline}} \cdot \left(\frac{R_1 \cdot \eta_{rel} + R_2 + R_3}{R_1 + R_2 + R_3}\right) \cdot \left(1 + \frac{R_1 + R_3}{R_1 \cdot \eta_{rel} + R_3}\right)$$

The Relative Viscosity expression is the same, but the Relative Flow expression changes.

For those embodiments that measure the pressure drop across $R_1$, and $R_2$, only, and have delay volume $D_2$ present, the Relative Viscosity and the Relative Flow expressions are:

$$\eta_{rel} = \frac{\eta}{\eta_0} = \frac{P3_{Baseline} \cdot (P_2 - P_3)}{P_3 \cdot (P2_{Baseline} - P3_{Baseline})}$$

$$Q_{rel} = \frac{Q}{Q_0} =$$

$$\frac{P_2 - P_3}{P2_{Baseline} P_3 + P3_{Baseline} \cdot P_2} \cdot \left(\frac{R_1 \cdot \eta_{rel} + R_2 + R_3}{R_1 + R_2 + R_3}\right) \cdot \left(1 + \frac{R_1 + R_3}{R_1 \cdot \eta_{rel} + R_3}\right)$$

If $D_2$ is removed, the Relative Viscosity expression is the same, but the Relative Flow expression changes to:

$$Q_{rel} = \frac{Q}{Q_0} =$$

$$\frac{P_2 - P_3}{P2_{Baseline} P_3 + P3_{Baseline} \cdot P_2} \cdot \left(\frac{R_1 + R_2 + R_3 \cdot \frac{1}{\eta_{rel}}}{R_1 + R_2 + R_3}\right) \cdot \left(1 + \frac{R_1 + R_3}{R_1 \cdot \eta_{rel} + R_3}\right)$$

Finally, for those embodiments that measure the pressure drop across $R_1$ and $R_3$, only, and have delay volume $D_2$ present, the Relative Viscosity and the Relative Flow expressions are:

$$\eta_{rel} = \frac{\eta}{\eta_0} = \frac{P_1 \cdot P3_{Baseline}}{P_3 \cdot P1_{Baseline}}$$

-continued $$Q_{rel} = \frac{Q}{Q_0} = \frac{P3}{P3_{Baseline}} \cdot \left(\frac{R_1 \cdot \eta_{rel} + R_2 + R_3}{R_1 + R_2 + R_3}\right)$$

If $D_2$ is removed, the Relative Viscosity expression is the same, but the Relative Flow expression changes to:

$$Q_{rel} = \frac{Q}{Q_0} = \frac{P3}{P3_{Baseline}} \cdot \left(\frac{R_1 + R_2 + R_3 \cdot \frac{1}{\eta_{rel}}}{R_1 + R_2 + R_3}\right)$$

Experimental Results

FIGS. 9 through 14 show chromatograms obtained using the preferred embodiment of FIG. 8. Except as noted, the analytical conditions are:

| | |
|---|---|
| Solvent | THF (Tetrahydrofuran) |
| Flow | 1 ml/min |
| Pump type | Dual piston with 50 ul heads |
| | Waters Model 616, Milford, MA |
| Pump fluid filter | None |
| Viscometer temperature | 40° C. |
| Colunm oven temperature | 40° C. |
| Sample compartment temperature | 40° C. |
| Colunms | 2 Styragel ™ HT6E (7.8 × 300 mm) |
| | 1 Styragel ™ HT3 (7.8 × 300 mm) |
| Concentration of injected solutions: | |
| 2630 Mw standard | 0.41467% |
| 1260000 Mw standard | 0.032008% |
| NBS 706 standard | 0.055654% |
| Injection volume | 300 µl |
| Signal filter time constant | 1 second |

Figure 9:
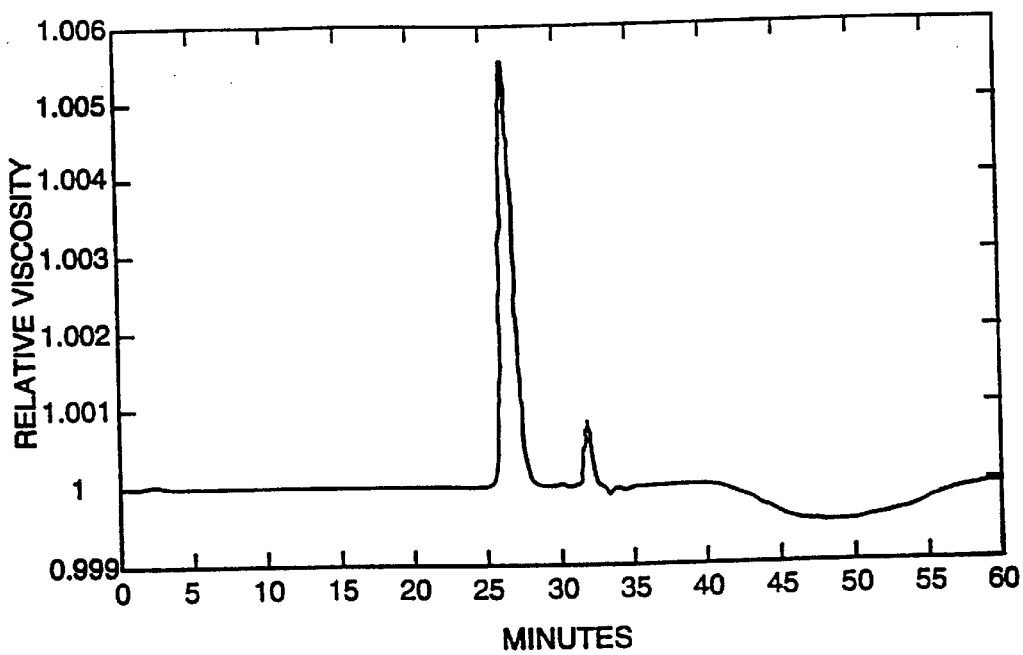
FIG. 9 is a Relative Viscosity chromatogram of a 2630 Mw narrow standard.
Figure 10:
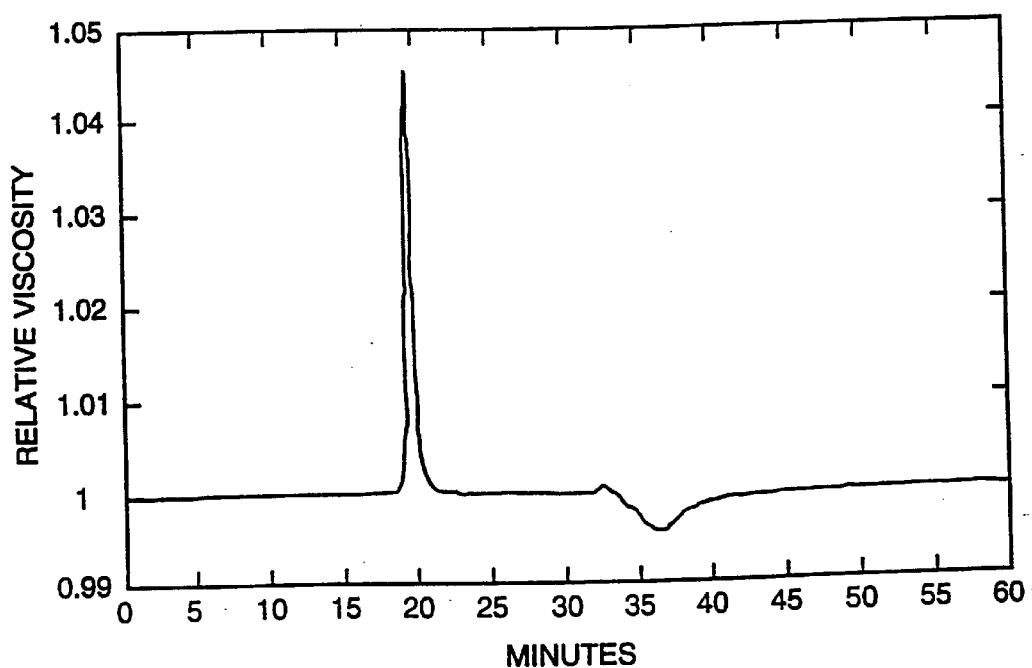
FIG. 10 is a Relative Viscosity chromatogram of a 1260000 Mw narrow standard.
Figure 11:
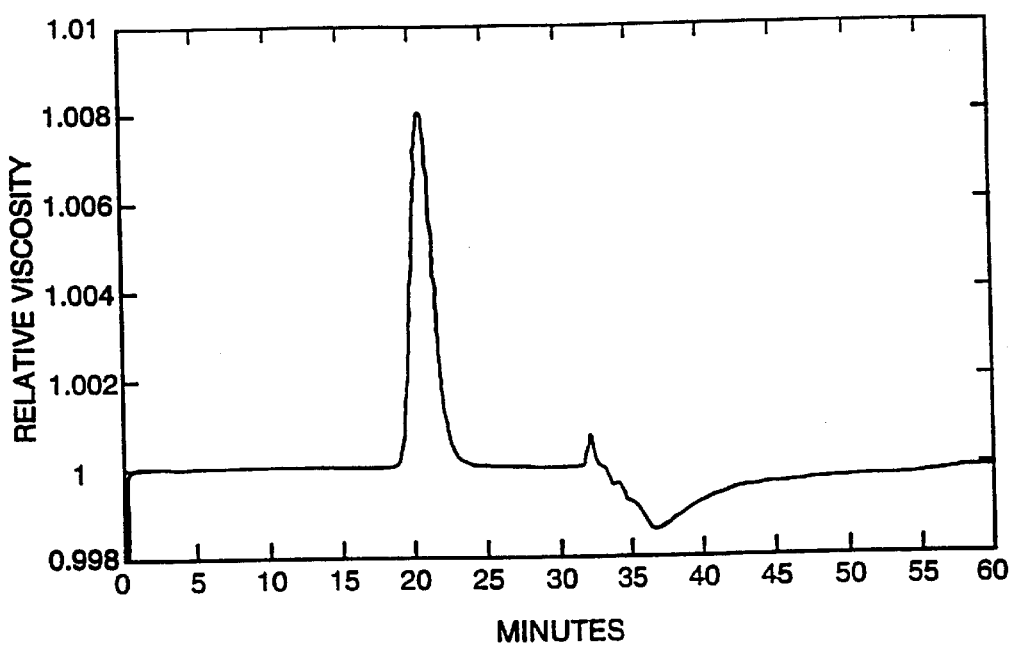
FIG. 11 is a Relative Viscosity chromatogram of a NBS 706 broad standard.

FIGS. 9, 10 and 11 show the Relative Viscosity chromatogram obtained with injections of standard solutions:

| | |
|---|---|
| FIG. 9 | 2630 molecular weight narrow standard |
| FIG. 10 | 1260000 molecular weight narrow standard |
| FIG. 11 | NBS 706 broad standard |

The signal to noise ratio of FIG. 9 is 275, FIG. 10 is 2280, and FIG. 11 is 415. The inverted "dips" in the chromatograms are due to the analytical peak going through R2 and R3.

To illustrate clearly the Relative Viscosity independence of flow changes, and also the benefits of the Relative Flow signal, the following experiment was performed. The solvent flow was decreased to 0.9 ml/min, and then an injection of the 2630 molecular weight solution was made. During the 60 minutes chromatogram, the flow was linearly increased back to 1 ml/min.

Figure 12:
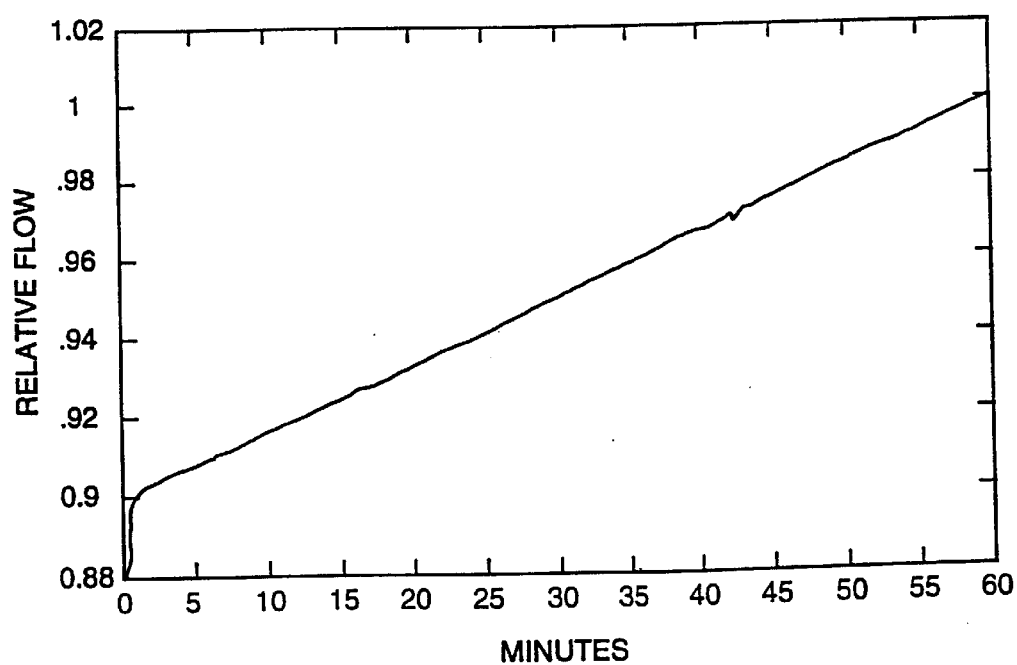
FIG. 12 is a Relative Flow chromatogram with a flow gradient.
Figure 13:
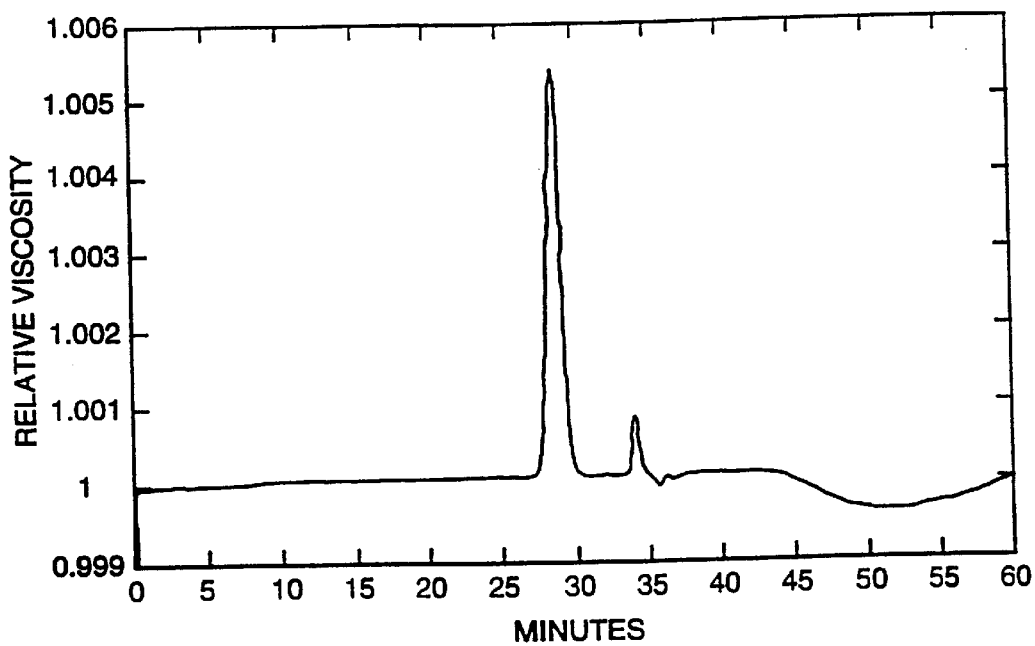
FIG. 13 is the Relative Viscosity chromatogram of a 2630 Mw narrow standard, with the same flow gradient of FIG. 12.

FIG. 12 shows the Relative Flow chromatogram, which exactly tracks the flow gradient. FIG. 13 shows the Relative Viscosity chromatogram, which amplitude is virtually unaffected by the flow gradient. However, the peak retention time is obviously affected by the flow gradient, and is clearly different to that of FIG. 9 chromatogram (about two minutes difference).

Figure 14:
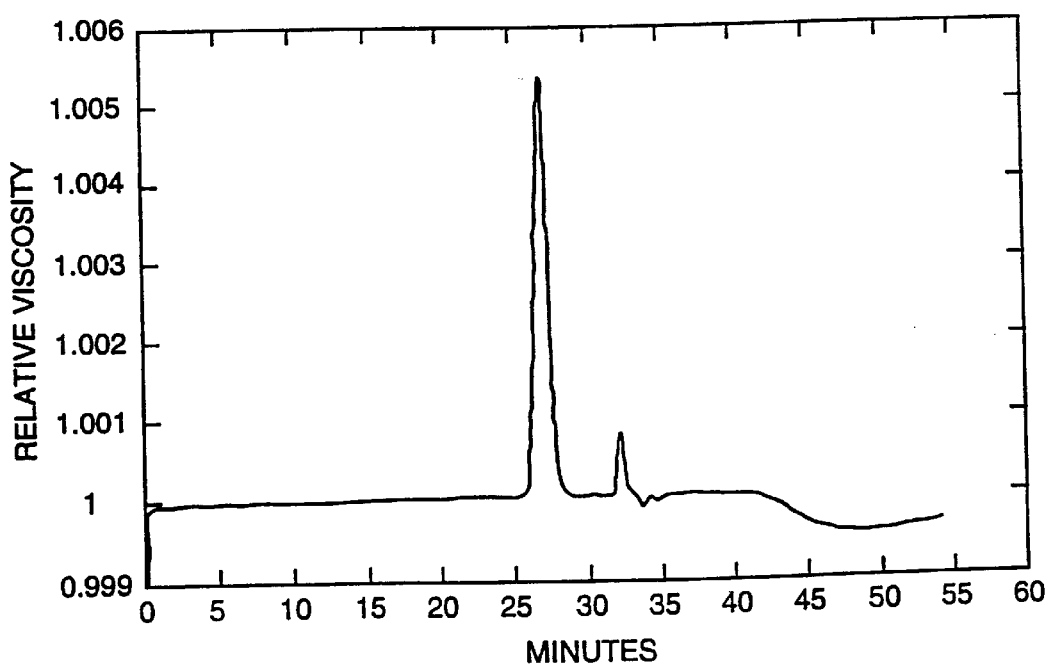
FIG. 14 is the Relative Viscosity chromatogram of FIG. 13, corrected in time using the Relative Flow chromatogram of FIG. 12.

Using the Relative Flow information in real time or in post-run processing, it is possible to relocate in time the peak of FIG. 13, so the retention time is as if the flow would have been constant at 1 ml/min. FIG. 14 shows the corrected Relative Viscosity chromatogram, which has a peak retention time equal to that of FIG. 9 chromatogram.

Figure 16:
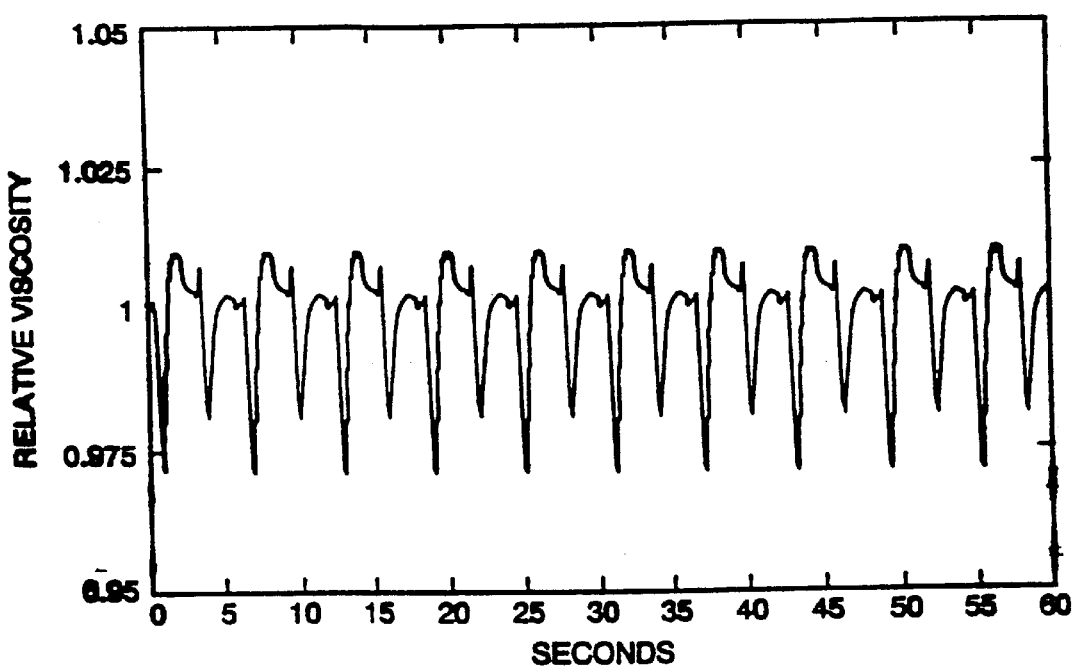
FIG. 16 is a relative viscosity baseline plot in a Three Capillary Flow Through Viscometer without a preprocessing algorithm according to the invention.
Figure 17:
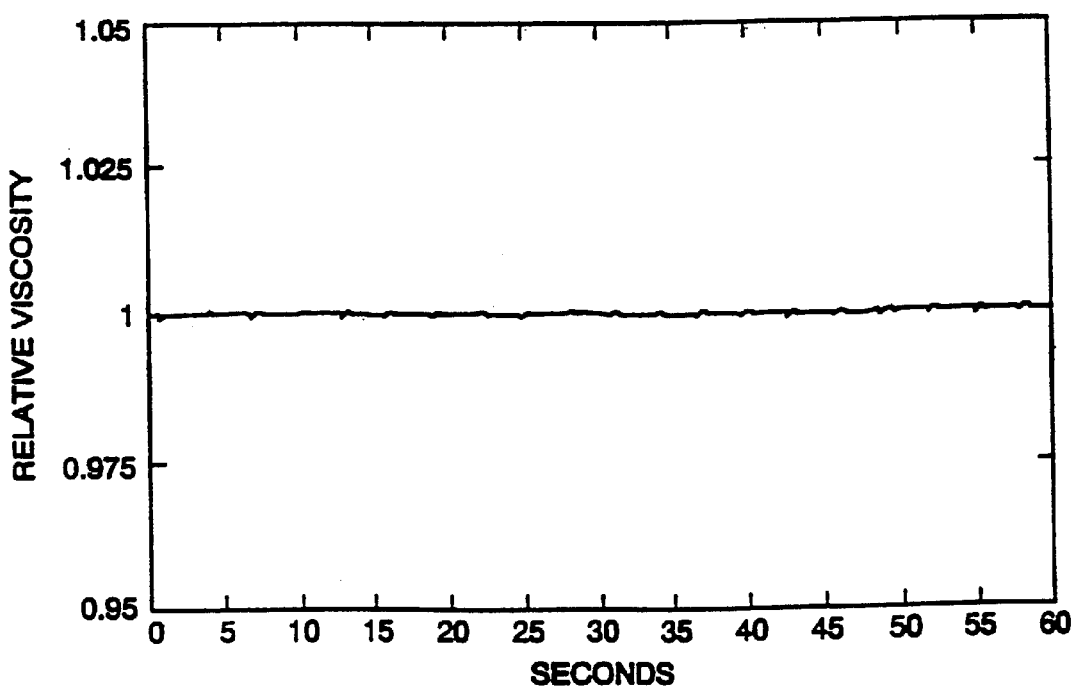
FIG. 17 is a relative viscosity baseline plot in a Three Capillary Flow Through Viscometer with the preprocessing algorithm according to the invention.

FIG. 16 shows the viscometer output of a multicapillary viscometer design without the present invention preprocessing method, and FIG. 17 shows the same viscometer output with the preprocessing method. The type of multicapillary viscometer used is the Three Capillary Flow Through Viscometer that delivers a Relative Viscosity output. The test conditions are summarized in the following table.

| | |
|---|---|
| Solvent | THF |
| Flow | 1 ml/min |
| Pump type | Dual piston with 50 µl heads |
| Pump fluid filter | None |
| Viscometer type | Three Capillary Flow Through |
| Viscometer temperature | 40 deg C. |
| Sample frequency | Ten samples per second |
| Number of equalization coefficients | 3 |
| Signal filter time constant | None |

A dual piston alternating pump without any fluid filter was connected directly to the viscometer, which illustrates arguably the worst possible condition for a capillary type viscometer. FIG. 16, in which the preprocessing method disclosed herein was not used, shows clearly the pump fast flow transients. FIG. 17, using the same plot scale as FIG. 16, demonstrates a reduction of more than 50 times in the pump pulsation transients when the preprocessing method is used.

The small disturbance still visible in the plot of FIG. 17 could be decreased using more than three coefficients in the dynamic equalization, leading to a further decrease in pump pulsation. However, three coefficients have been proved to be sufficient in practical applications.

EQUIVALENTS

Those skilled in the art will recognize, or using no more than routine experimentation, equivalents to the specific embodiments of the invention described specifically herein. Such equivalents are intended to be encompassed in the scope of the following claims.

I claim:

1. An apparatus for measuring the viscosity of a solution, comprising
   an input tube for transporting the solution, said solution having a flow Q;
   a flow splitter in fluid communication with and downstream from the input tube, for diverting the flow Q into flow streams Q1 and Q2;
   a first tube having a geometric resistance R1 located in stream Q1 downstream from the flow splitter;
   a delay volume D1 located in stream Q1 downstream from said first tube;
   a second tube having a geometric resistance R2 located in stream Q2 and downstream from the flow splitter,
   a third tube having a geometric resistance R3 located in stream Q1 and downstream from delay volume D1;
   a first transducer T1 having means to measure the pressure difference across said third tube, transducer T1 generating a signal proportional to the pressure difference across said third tube;
   a second transducer T2 having means to measure the pressure difference across said second tube, transducer T2 generating a signal proportional to the pressure difference across said second tube;
   signal handling means for processing the signals from transducers T1 and T2 and generating thereby the relative viscosity information for the solution, and the relative flow information for the solution flow.

2. The apparatus of claim 1 further comprising a second delay volume D2 located in stream Q2 downstream from the flow splitter.

3. The apparatus of claim 1 wherein at least one of the transducers is dead-ended.

4. The apparatus of claim 1 wherein the signal handling means comprises an analog to digital converter whose output is sent to a digital signal processor.

5. An apparatus for measuring the viscosity of a solution, comprising
- an input tube for transporting solution, said solution having a flow Q;
- a flow splitter in fluid communication with and downstream from the input tube, for diverting the flow Q into flow streams Q1 and Q2;
- a first tube having a geometric resistance R1 located in stream Q1 downstream from the flow splitter;
- a first delay volume D1 located in stream Q1 downstream from said first tube;
- a second delay volume D2 located in stream Q2 downstream from the flow splitter;
- a second tube having geometric resistance R2 located in stream Q2 and downstream from delay volume D2;
- a third tube having geometric resistance R3 located in stream Q1 and downstream from delay volume D1;
- a first flow-through transducer T1 having hydraulic connections located in stream Q1, the connections being located so as to measure the pressure difference across said third capillary, transducer T1 generating a signal proportional to the pressure difference across said third tube;
- a second flow-through transducer T2 having hydraulic connections located in stream Q2, the connections being located so as to measure the pressure difference across said second tube, transducer T2 generating a signal proportional to the pressure difference across said second tube;
- signal handling means for processing the signals from transducers T1 and T2 and generating thereby the relative viscosity information for the solution, or the relative flow information for the solution flow.

6. An apparatus for measuring the viscosity of a solution, comprising
- an input tube for transporting the sample solution having a flow Q;
- a flow splitter in fluid communication with and downstream from the input tube, for diverting the flow Q into flow streams Q1 and Q2;
- a first tube having a geometric resistance R1 located in stream Q1 downstream from the flow splitter;
- a delay volume D1 located in stream Q1 downstream from said first tube;
- a second tube having a geometric resistance R2 located in stream Q2 and downstream from the flow splitter;
- a third tube having a geometric resistance R3 located in stream Q1 and downstream from delay volume D1;
- a first transducer T1 having means to generate a signal proportional to the pressure difference across said first tube;
- a second transducer T2 having means to generate a signal proportional to the pressure difference across said second tube;
- signal handling means for processing the signals from transducers T1 and T2 and generating thereby the relative viscosity information for the solution, or the relative flow information for the solution flow.

7. The apparatus of claim 6 further comprising a second delay volume D2 located in stream Q2 downstream from the flow splitter.

8. The apparatus of claim 6 wherein at least one of the transducers is dead-ended.

9. The apparatus of claim 6 wherein the signal handling means comprises an analog to digital converter whose output is sent to a digital signal processor.

* * * * *